United States Patent [19]
Cover et al.

[11] Patent Number: 5,876,943
[45] Date of Patent: Mar. 2, 1999

[54] HELICOBACTER TAGA GENE FUSION PROTEIN

[75] Inventors: Timothy L. Cover; Martin J. Blaser, both of Nashville, Tenn.; Harry Kleanthous, Cambridge, Mass.; Murali K. R. Tummuru, Nashville, Tenn.

[73] Assignee: Vanderbilt University, Nashville, Tenn.

[21] Appl. No.: 34,306

[22] Filed: Mar. 2, 1998

Related U.S. Application Data

[63] Continuation of Ser. No. 316,397, Sep. 30, 1994, Pat. No. 5,733,340, which is a continuation-in-part of Ser. No. 53,614, Apr. 26, 1993, Pat. No. 5,403,924, which is a continuation-in-part of Ser. No. 959,940, Oct. 13, 1992, abandoned.

[51] Int. Cl.$^6$ ..................................................... C12Q 1/68
[52] U.S. Cl. ......................... 435/6; 435/7.32; 435/320.1; 536/23.1
[58] Field of Search ........................... 435/6, 7.32, 320.1; 536/23.1

[56] References Cited

U.S. PATENT DOCUMENTS

| | | | |
|---|---|---|---|
| 5,262,156 | 11/1993 | Alemohammad | 424/92 |
| 5,403,924 | 4/1995 | Cover et al. | 536/23.1 |
| 5,733,740 | 3/1998 | Cover et al. | 435/7.32 |

FOREIGN PATENT DOCUMENTS

| | | |
|---|---|---|
| WO 93/18150 | 9/1993 | WIPO . |
| WO 94/09023 | 4/1994 | WIPO . |

OTHER PUBLICATIONS

Covacci et al. "Molecular characterization of the 128–kDa immunodominant antigen of *Helicobacter pylori* associated with cytotoxicity and dunodenal ulcer" *Proc. Natl. Acad. Sci. USA0* 90:5791–5795, Jun. 1993.

Tummuru et al. "Cloning and Expression of a High–Molecular–Mass Major Antigen of *helibacter pylori*: Evidence of Linkage to Cytotoxin Production" *Infec. ADnd Immunol.* 61(5):1799–1809, May 1993.
Xiang et al. *Lancet* 1:900–901, 1993.
Crabtree et al. *J. Clin. Pathol.* 45:733–734, 1992.
Gerstenecker et al. *Eur. J. Clin. Microbiol. Infect. Dis.* 11(70:595–601, Jul. 1992.
Timothy L. Cover and Martin J. Blaser *J. Biol. Chem.* 267(15):10570–10575, 1991.
Cover et al. *J. Clin. Investig.* 90:913–918, 1992.
Parsonnet et al. *N. Eng. J. Med.* 325(16):1127–1131, Oct. 1991.
Nomura et al. *N. Eng. J. Med.* 325:1132–1136, Oct. 1991.
Crabtree et al. *Digestive Diseases & Sciences* 36(9):1266–1273, Sep. 1991.
Crabtree et al. *Lancet* 338:332–335, Aug. 1991.
Cover et al. *Infect. and Immun.* 59(4):1264–1270, Apr. 1991.
Cover et al. *Infect. and Immun.* 58(3):603–610, 1990.

(List continued on next page.)

*Primary Examiner*—James C. Housel
*Assistant Examiner*—Ginny Allen Portner
*Attorney, Agent, or Firm*—Needle & Rosenberg

[57] ABSTRACT

The present invention provides an isolated nucleic acid encoding an approximately 120–128 kilodalton antigen of *Helicobacter pylori*, or an antigenic fragment thereof, wherein the antigen is associated with peptic ulceration. The present invention also provides methods of detecting the presence of a *Helicobacter pylori* strain possessing the 120–128 kilodalton antigen in a subject, comprising the steps of contacting an antibody-containing sample from the subject with a detectable amount of the tagA antigen or antigenic polypeptide of the present invention and detecting the binding of the antigen or fragment and the antibody. The detection of a strain expressing the TagA antigen is an indication of predisposition to peptic ulceration and gastric carcinoma. A mutant *H. pylori* not expressing a functional TagA antigen is also provided.

2 Claims, 4 Drawing Sheets

OTHER PUBLICATIONS

Hirschl et al. *J. Clin. Pathol.* 43:511–513, 1990.
Figura et al. *Clin. Microbiol.* 27(1):225–226, Jan. 1989.
Leunk et al. *J. Med. Microbiol.* 26:93–99, 1988.
Apel et al. *Zbl. Bakt. Hyg.* A268:271–276, 1988.
von Wulffen et al. *J. Clin. Pathol.* 41:653–659, 1988.
Covacci et al. *Eur.J. Clin. Microbiol. & Infect. Dis.* 12(10):739–745, 1993.
Halter et al. *BioMed* 65(6):625–638, Nov.–Dec., 1992.
Andersen et al. *J. Clin. Microbiol.* 30(7):1743–1751, Jul. 1992.
Kosunen, Tu et al. *Lancet* 339, 893–895, Apr. 11, 1992.
Goossens et al. *J. Clin. Microbiol.* 30(1):176–180, Jan. 1992.
Van Wulffen, H. *FEMS Microbiol. Letters,* 42:129–133, 1987.

HELICOBACTER TAGA GENE FUSION PROTEIN

This application is a continuation of, and claims the benefit of, application Ser. No. 08/316,397, filed Sep. 30, 1994, now U.S. Pat. No. 5,733,340 which is a Continuation-in-Part of Ser. No. 08/053,614, filed Apr. 26, 1993, now U.S. Pat. No. 5,403,924, issued Apr. 4, 1995, which is a Continuation-in-Part of Ser. No. 07/959,940, filed Sep. 13, 1992, now abandoned, which applications are hereby incorporated herein by reference.

BACKGROUND OF THE INVENTION

Helicobacter pylori is now recognized as an important pathogen of humans in that the chronic gastritis it causes is a risk factor for the development of peptic ulcer disease. There is also increasing evidence that persistent infection with Helicobacter pylori is a risk factor for the development of gastric adenocarcinoma (1,2), especially of the distal stomach (3–5). The evidence comes mainly from epidemiologic investigations (6–9), including nested case-control studies (4,5,10), and molecular and pathological studies support its biological plausibility (11). However, although essentially all infected persons develop gastritis, clinical consequences of H. pylori infection are recognized in only a minority of persons. Also, while H. pylori infection is highly prevalent in patients with gastric cancer, most H. pylori-infected persons never develop these neoplasms (12). Thus, it is important to identify other factors that more precisely determine risk among H. pylori-infected persons.

H. pylori strains are highly diverse (13–15) at a genetic level, but most phenotypic characteristics are well-conserved. Furthermore, individuals can be infected with more than one strain (4,15). Thus, it is important to isolate particular characteristics of H. pylori strains that might affect risk of gastric cancer development.

Two exceptions to the phenotypic homogeneity are currently recognized. First, about 50%–60% of H. pylori strains produce a vacuolating cytotoxin in vitro (20,39), and toxin production is associated with peptic ulceration (40). Second, there is heterogeneity in whether an antigenic protein migrating at approximately 120–128 kilodalton (kDa) on reducing sodium dodecyl sulfate-polyacrylamide gel electrophoresis [SDS-PAGE] is produced (20). More recent measurements of this protein (referred to interchangably as TagA or CagA) have yielded molecular weights as high as 140 kDa. Although toxic activity is mediated by an 87 kDa protein (23,41), toxin production itself is associated with the presence of the antigenic 120–128 kDa protein (20). Previous studies have found that about 60–80% of H. pylori isolates express the 120–128 kDa protein (20,42). Notably, presence of antibodies to the 120–128 kDa protein in either serum or mucosal secretions is associated with the presence of peptic ulceration (18,20).

Until now, little was known about the association between toxin production, ulcers or gastric carcinoma and the 120–128 kDa antigen. This is due to the previous inability to further characterize the 120–128 kDa antigen after its initial visualization.

In previous studies, the 120–128 kDa antigen was visualized by Western blotting, but virtually no other characterization was performed (20). In contrast to the ease with which this antigen has been visualized by Western blotting, the 120–128 kDa band has not been easily visualized by other methods such as silver staining (FIG. 2 in Cover et al., 1990 (20)). The explanation for this phenomenon is that this antigen is present only in minute quantities, relative to other H. pylori proteins. Recently, Gerstenecker et al. (43) have reported the isolation of an approximately 120 kDa protein from H. pylori which reacts with positive human control serum. However, virtually no characterization (such as N-terminal sequencing) of this antigen has been performed.

Despite the difficulty of purification, the present invention provides the cloning and sequence of the gene and deduced amino acid sequence encoding the 120–128 kDa protein. This data was obtained using alternate methodology that did not require purification of the 120–128 kDa antigen. The invention also provides diagnostic, therapeutic, and prophylactic compositions and methods.

Immunoblot studies suggest that persons infected with tagA+ strains have higher degrees of gastric inflammation and epithelial cell damage than do persons from whom tagA− strains have been isolated (18). Persons infected with tagA+ H. pylori strains have enhanced expression of IL-1α, IL-1β, and IL-8 in gastric biopsies, compared to uninfected persons, and patients infected with tagA− strains (19). Both intensity of inflammation and epithelial damage may be involved in the pathogenesis of gastric cancer (1). Thus, there is a need to examine the importance of tagA expressing H. pylori strains in this context.

The invention meets these needs by providing a new serologic assay based on a recombinant fragment of tagA, and a method of determining predisposition to gastric cancer.

SUMMARY OF THE INVENTION

The present invention provides an isolated nucleic acid encoding an approximately 120–128 kilodalton antigen of Helicobacter pylori, or an antigenic fragment thereof, wherein the antigen is associated with peptic ulceration and gastric carcinoma. The present invention also provides methods of detecting the presence of a Helicobacter pylori strain possessing the 120–128 kilodalton antigen in a subject, comprising the steps of contacting an antibody-containing sample from the subject with a detectable amount of the TagA antigen or fragment thereof of the present invention and detecting the reaction of the fragment and the antibody.

DETAILED DESCRIPTION OF THE INVENTION

Nucleic Acids

Figure 1:
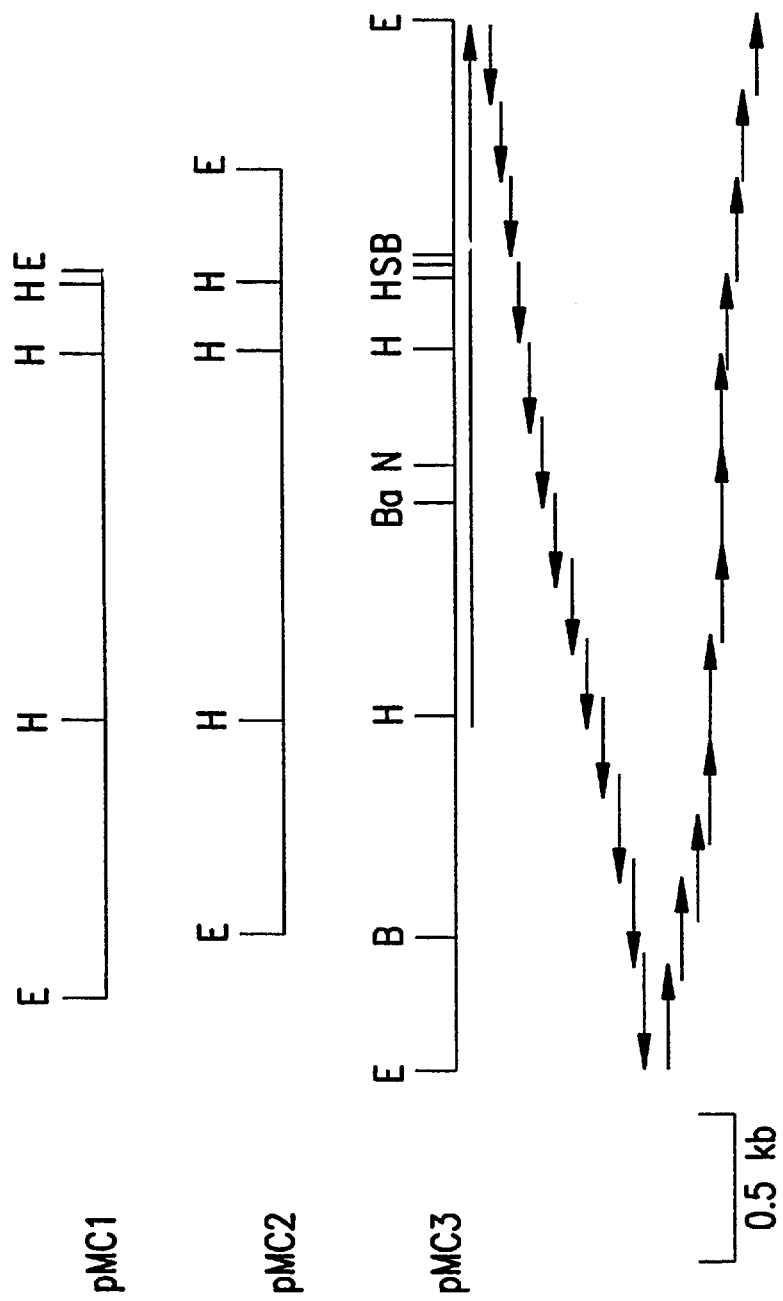
FIG. 1 shows physical maps of plasmids pMC1, pMC2, and pMC3. The large arrow beneath pMC3 represents the location of the tagA gene and the direction of transcription as determined by deletion mutations and immunoblotting. The small arrows represent the strand and extent of DNA sequenced from exonuclease III-derived fragments. Restriction endonuclease cleavage sites: B, BglII; Ba, BamHI; E, EcoRI; H, HindIII; N, NdeI; S, SacI.

The present invention provides an isolated nucleic acid encoding an approximately 120–128 kDa antigen or fragment of H. pylori, associated with peptic ulceration (TagA). By "isolated" is meant sufficiently separated from other nucleic acids, proteins and other cellular components found in the naturally occurring organism to be useful in a clinical diagnostic or other scientific protocol. The nucleic acid encoding the 120–128 kDa antigen can be the native tagA gene, which is specific for strains of H. pylori expressing the 120–128 kDa antigen. By "specific" is meant an isolated sequence which does not hybridize to a significant degree above background with nucleic acids from H. pylori strains that do not express the antigen.

An example of such an isolated nucleic acid is an open reading frame of 3543 base pairs comprising nucleotides 1072 through 4614 contained in a 4821 base pair insert (SEQ ID NO:3). A cell line containing a plasmid having the full length tagA gene is deposited with the American Type Culture Collection (1230 Parklawn Drive, Rockville Md. 20852) under ATCC Accession No. 69273. This isolated H. pylori-specific nucleic acid can be used to detect H. pylori expressing the 120–128 kDa antigen in methods such as polymerase chain reaction (PCR), ligase chain reaction and hybridization as further described below. The nucleic acid or fragments thereof can be in a suitable expression vector and host, and utilized to produce the full length TagA protein as further described herein.

An example of a nucleic acid encoding an antigenic fragment of the 120–128 kDa antigen is a truncated open reading frame of 2577 base pairs comprising nucleotides 1072 through 3648 contained in a 3648 base pair insert (SEQ ID NO:1). This specific nucleic acid can be used to detect H. pylori possessing the 120–128 kDa antigen in methods such as polymerase chain reaction, ligase chain reaction and hybridization. Alternatively, the 3648 base pair sequence can be in a vector in a suitable host and utilized to produce an antigenic fragment of TagA.

Another example of a nucleic acid encoding an antigenic fragment of the 120–128 kDa antigen is a recombinant fragment (orv220) of the tagA gene comprising nucleotides 1921 through 3648 of SEQ ID Nos:1 and 3 (Example 4). This specific nucleic acid can be used to detect H. pylori strains expressing the 120–128 kDa antigen in methods such as polymerase chain reaction, ligase chain reaction and hybridization. Alternatively, the nucleic acid can be in a vector in a suitable host and utilized to produce an antigenic fragment of TagA.

Nucleic acids encoding other antigenic fragments of TagA can be obtained by the skilled artisan using routine methods and a routine amount of experimentation following the procedures described herein for obtaining the exemplary nucleic acids. Other methods for obtaining nucleic acid fragments of a known isolated nucleic acid, such as restriction digests, can be applied to the larger coding sequence to obtain nucleic acids encoding other fragments of the antigen. The nucleic acids so obtained can be routinely screened for antigenicity, specificity, etc., according to the examples herein.

Changes in the nucleotide sequence of the exemplary nucleic acids encoding TagA or antigenic fragments thereof are also contemplated as long as the antigenicity of the polypeptide encoded by the nucleic acids is maintained. Likewise, nucleic acids used as primers or probes can have substitutions so long as enough complementary bases exist for selective or specific hybridization (44).

Another example of the nucleic acid encoding the TagA antigen is an alternative coding sequence for the antigen, obtained based on the degeneracy of the genetic code. Having provided one amino acid sequence of the TagA antigen (SEQ ID NO:3), the skilled artisan can determine the nucleotide sequence that encodes the antigen or a fragment of the antigen, and can generate the nucleic acid using the existing techniques.

An isolated nucleic acid that selectively hybridizes with the nucleic acid comprising nucleotides 1072 through 4614 contained in the nucleotide sequence defined in the Sequencing Listing as SEQ ID NO:3 under polymerase chain reaction conditions is also contemplated. The term "selectively" as used herein refers to a nucleic acid that will hybridize under PCR conditions with the reference nucleic acid at a level distinguishable from background or random hybridization, but may also hybridize with selected other nucleic acids at a level clearly distinguishable over background or random hybridization. The selectively hybridizing nucleic acid can be complementary to the above nucleic acid. The degree of sequence identity and length of the hybridizing sequences can be selected based on the intended use of the particular sequence. If used as primers, the invention provides compositions including at least two nucleic acids which selectively hybridize with different regions so as to amplify a desired region. Exemplary PCR conditions are provided herein, are well known in the art, and are taught by the providers of PCR reagents and apparatus.

An isolated nucleic acid that specifically hybridizes with the nucleic acid comprising nucleotides 1072 through 4614 contained in the nucleotide sequence defined in the Sequencing Listing as SEQ ID NO:3 under the stringency conditions of 68° C. for 16 hours in buffer containing 6x SSC, 0.5% sodium dodecyl sulfate, 5x Denhardt's solution, with washing at 60° C. in 0.5x SSC is also contemplated (Example 1, southern hybridization). Other examples of hybridization conditions are also provided. Specific hybridization conditions exclude nucleic acids that hybridize with nucleic acids other than the reference nucleic acid. Thus, the hybridizing nucleic acid can be complementary to a segment of or all of the above nucleic acid, or it can have sufficient complementarity with the segment to which it hybridizes to prevent it from binding to other naturally occurring nucleic acids. The sequences to which the nucleic acid will hybridize can be selected based on the nucleotide sequence and the utility of the particular sequence. For example, the specifically hybridizing nucleic acids can be used as probes for detecting the presence of an organism that has the nucleic acid to which it hybridizes. Alternatively, the hybridizing nucleic acids can encode the fragments of TagA provided herein.

Also provided is an isolated nucleic acid that hybridizes with the nucleic acid encoding the H. pylori TagA under stringent conditions and has at least 70% complementarity with the segment and strand of the nucleic acid of SEQ ID NO:3 to which it hybridizes. The hybridizing nucleic acids of the invention can have at least 70%, 80%, 85%, 90%, 95%, 97%, 98% and 99% complementarity with the segment and strand of the exemplary sequence to which it hybridizes. The nucleic acids can range from at least 18 to 4000 nucleotides in length. Thus, the nucleic acid can encode TagA from another tagA+ strain, or can be used as a probe or primer for detecting the presence of tagA+ H pylori.

The invention provides examples of these nucleic acids of H. pylori, so that the degree of complementarity required to distinguish specifically hybridizing from nonspecifically hybridizing nucleic acids under specific conditions can be clearly determined for each nucleic acid. The nucleic acids can be double stranded or single stranded depending on the intended use (e.g. as a coding sequence or a primer/probe, respectively). It should also be clear that a specifically hybridizing nucleic acid will not hybridize with nucleic acids encoding unrelated proteins.

One skilled in the art can readily obtain the nucleic acids of the present invention using routine methods to synthesize a full gene as well as shorter nucleotide fragments. For example, techniques for obtaining nucleic acids such as those provided in the Sequence Listing are specifically provided in the application. Furthermore, additional methods are provided in the art that can be utilized without significant modification. Ferretti et al. (75) and Wosnick et al. (76) show routine methods to synthesize a gene of known sequence. More specifically, Ferretti et al. teach the synthesis of a 1057 base pair synthetic bovine rhodopsin gene from synthetic oligonucleotides. The synthesized gene was faithful to the known sequence (first sentence, page 603), demonstrating the reliability of this method of gene synthesis. Additionally, Wosnick et al. teach the synthesis of a maize glutathione-transferase (GST) gene using an efficient, one-step annealing/ligation protocol. This technique also produced a complete synthetic gene with 100% fidelity, which demonstrates the routine nature of this protocol.

Antigen

Purified antigenic polypeptides encoded by the nucleic acids of the present invention are also contemplated. As used herein, "purified" means the antigen is sufficiently free of contaminants or cell components with which the antigen normally occurs to distinguish the antigen from the contaminants or components. Thus, the purified antigenic polypeptide is sufficiently separated from contaminants, so that it can be used in a clinical diagnostic or other laboratory protocol. The purified approximately 120–128 kDa full-length antigen and antigenic fragments of the present invention are also referred to herein as "the antigen," "the TagA antigen" or "the cagA antigen."

Specifically, an approximately 130 kDa full length TagA antigenic polypeptide (SEQ ID NO:4) is encoded by an open reading frame of 3543 base pairs within the 4821 base pair cloned insert, consisting essentially of the amino acids encoded by nucleotides 1072 through 4614 contained in the nucleotide sequence defined in the Sequence Listing as SEQ ID NO:3.

An approximately 96 kDa antigenic fragment of TagA is encoded by an open reading frame of 2577 base pairs within the 3648 base pair cloned insert, consisting essentially of the amino acids encoded by nucleotides 1072 through 3648 contained in the nucleotide sequence defined in the Sequence Listing as SEQ ID NO:1.

Another antigenic fragment of TagA is encoded by an open reading frame (orv220), consisting essentially of the amino acids encoded by nucleotides 1921 through 3648 contained in the nucleotide sequence defined in the Sequence Listing as SEQ ID NO:1.

An antigenic fragment of the antigen can be selected by applying the routine technique of epitope mapping to the TagA protein to determine the regions of the protein that contain epitopes reactive with serum antibodies or capable of eliciting an immune response in an animal. Once the epitope is selected, an antigenic polypeptide containing the epitope can be synthesized directly, or produced recombinantly by cloning nucleic acids encoding the polypeptide in an expression system, according to the standard methods. Alternatively, an antigenic fragment of the antigen can be isolated from the whole antigen or a larger fragment by chemical or mechanical disruption. The purified fragments thus obtained can be tested to determine their antigenicity and specificity by the methods taught herein. An antigenic fragment is defined as an amino acid sequence of at least about 5 consecutive amino acid derived from the antigen amino acid sequence that is reactive with (binds) an antibody.

Once the amino acid sequence of the antigenic polypeptide is provided, antigenic polypeptides can be designed that correspond to amino acid sequences of the native antigen, but with modifications in the form of substitutions, inclusions or deletions of particular amino acid residues in the derived sequences. The modifications can include attaching the antigen to sequences designed to provide for some additional property, such as solubility. The modifications can include other amino acids that provide for some additional property, such as to remove/add amino acids capable of disulfide bonding, to increase bio-longevity, alter enzymatic activity, or alter interactions with gastric acidity. In any case, the peptide must possess a bioactive property, such as antigenicity, immunogenicity, specificity etc. The polypeptides so designed can be tested for antigenicity, immunogenicity and specificity by the methods used and described herein. These polypeptides can then be synthesized, using standard peptide synthesis techniques. Thus, synthesis or purification of an extremely large number of polypeptides derived from the exemplary sequence of the TagA antigen is possible.

Determining Immunogenicity

The purified antigenic polypeptides can be tested to determine their immunogenicity and specificity. Briefly, various concentrations of a putative immunogenically specific fragment are prepared and administered to an animal and the immunological response (e.g., the production of antibodies or cell mediated immunity) of an animal to each concentration is determined. The amounts of antigen administered depend on the subject, e.g. a human or a guinea pig, the condition of the subject, the size of the subject, etc. Thereafter an animal so inoculated with the antigen can be exposed to the bacterium to determine the vaccine effect of the specific antigenic fragment. The specificity of the fragment can be ascertained by testing sera, other fluids or lymphocytes from the inoculated animal for cross reactivity with other closely related bacteria.

Vectors and Hosts

A vector comprising the nucleic acids of the present invention is also provided. The vectors of the invention can be in a host suitable for expressing the polypeptides encoded by the nucleic acid. Specific example of vectors and hosts are provided below in the Examples.

There are numerous E. coli expression vectors known to one of ordinary skill in the art useful for the expression of the antigen. Other microbial hosts suitable for use include bacilli, such as *Bacillus subtilus*, and other Enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary an amino terminal methionine can be provided by insertion of a Met codon 5' and in-frame with the antigen. Also, the carboxy-terminal extension of the antigen can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MFα-1 gene) is routinely used to direct protein secretion from yeast (45). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast.

Mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal. The vectors can contain genes conferring either gentamicin or methotrexate resistance for use as selectable markers. The antigen and immunoreactive fragment coding sequence can be introduced into a Chinese hamster ovary cell line using a methotrexate resistance-encoding vector. Presence of the vector DNA in transformed cells can be confirmed by Southern analysis and production of an RNA corresponding to the antigen coding sequence can be confirmed by Northern analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the DNA segments of interest can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Alternative vectors for the expression of antigen in mammalian cells, those similar to those developed for the expression of human gamma-interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted DNAs in mammalian cells (such as COS7).

The DNA sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired DNA sequences (see, e.g., U.S. Pat. No. 4,704,362).

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

Purified Antibodies

A purified monoclonal antibody that specifically binds the TagA antigen or antigenic fragment is also provided. The antibody can specifically bind a unique epitope of the antigen it can also bind epitopes of other organisms. The term "bind" means the well understood antigen/antibody binding as well as other nonrandom association with an antigen. "Specifically bind" as used herein describes an antibody or other ligand that does not cross react substantially with any antigen other than the one specified, in this case, the TagA antigen. Antibodies can be made as described in the Examples (see also, Harlow and Lane (46)). Briefly, purified antigen can be injected into an animal in an amount and in intervals sufficient to elicit an immune response. Polyclonal antibodies can be purified directly, or spleen cells from the animal can be fused with an immortal cell line and screened for monoclonal antibody secretion. Thus, nonhuman polyclonal antibodies that specifically bind the antigen are within the scope of the present invention.

A ligand that specifically binds the antigen is also contemplated. The ligand can be a fragment of an antibody or a smaller molecule designed to bind an epitope of the TagA antigen. The antibody or ligand can be bound to a substrate or labeled with a detectable moiety or both bound and labeled. The detectable moieties contemplated with the composition of the present invention are those listed below in the description of the diagnostic methods, including fluorescent, enzymatic and radioactive markers.

Antigen Bound to Substrate

A purified TagA antigen bound to a substrate is also provided. The antigen can also be bound to a purified antibody or ligand. The antibody can be a monoclonal antibody obtained by standard methods and as described herein.

Serological Detection (Diagnosis) Methods
   Detecting Antibody with Antigen
   The present invention provides a method of detecting the presence of a *H. pylori* strain possessing the 120–128 kDa antigen in a subject, comprising the steps of contacting an antibody-containing sample from the subject with a detectable amount of the TagA or TagA antigenic fragment of the present invention and detecting the binding reaction of the TagA or fragment and the antibody produced by the subject, the binding indicating the presence of the toxic *H. pylori* strain or previous infection with the toxic *H. pylori* strain. There are numerous routine immunological assays that can be used in the present detection and predisposition methods. Examples are provided below.
   Detecting Antigen with Antibody/Ligand
   One example of the method of detecting *H. pylori* possessing the antigen is performed by contacting a fluid or tissue sample from the subject with an amount of a purified antibody specifically reactive with the antigen, and detecting the binding of the antibody with the antigen. It is contemplated that the antigen will be on intact cells containing the antigen, or will be fragments of the antigen. As contemplated herein, the antibody includes any ligand which binds the antigen, for example, an intact antibody, a fragment of an antibody or another reagent that has reactivity with the antigen. The fluid sample of this method can comprise any body fluid which would contain the antigen or a cell containing the antigen, such as blood, plasma, serum, saliva and urine. Other possible examples of body fluids include sputum, mucus, gastric juice and the like.
   ELISA
   Immunoassays such as immunofluorescence assays (IPA), enzyme linked immunosorbent assays (ELISA) and immunoblotting can be readily adapted to accomplish the detection of the antigen. An ELISA method effective for the detection of the antigen can, for example, be as follows: (1) bind the antibody to a substrate; (2) contact the bound antibody with a fluid or tissue sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect antibody as well as antigen.
   Competitive Inhibition Assay
   Another immunologic technique that can be useful in the detection of *H. pylori* expressing tagA or previous *H. pylori* infection utilizes monoclonal antibodies (MAbs) for detection of antibodies specifically reactive with TagA antigen. Briefly, sera or other body fluids from the subject is reacted with the antigen bound to a substrate (e.g. an ELISA 96-well plate). Excess sera is thoroughly washed away. A labeled (enzyme-linked, fluorescent, radioactive, etc.) monoclonal antibody is then reacted with the previously reacted antigen-serum antibody complex. The amount of inhibition of monoclonal antibody binding is measured relative to a control (no patient serum antibody). The degree of monoclonal antibody inhibition is a very specific test for a particular variety or strain since it is based on monoclonal antibody binding specificity. MAbs can also be used for detection directly in cells by IFA.
   Micro-Agglutination Assay
   A micro-agglutination test can also be used to detect the presence of the TagA-possessing *H. pylori* strain in a subject. Briefly, latex beads (or red blood cells) are coated with the antigen and mixed with a sample from the subject, such that antibodies in the tissue or body fluids that are specifically reactive with the antigen crosslink with the antigen, causing agglutination. The agglutinated antigen-antibody complexes form a precipitate, visible with the naked eye or by spectrophotometer. In a modification of the above test, antibodies specifically reactive with the antigen can be bound to the beads and antigen in the tissue or body fluid thereby detected.
   Sandwich Assay/Flow Cytometry/Immunoprecipitation
   In addition, as in a typical sandwich assay, the antibody can be bound to a substrate and reacted with the antigen. Thereafter, a secondary labeled antibody is bound to epitopes not recognized by the first antibody and the secondary antibody is detected. Since the present invention provides TagA antigen for the detection of toxic *H. pylori* or previous *H. pylori* infection other serological methods such as flow cytometry and immunoprecipitation can also be used as detection methods.
   In the diagnostic methods taught herein, the antigen can be bound to a substrate and contacted by a fluid sample such as serum, urine, saliva or gastric juice. This sample can be taken directly from the patient or in a partially purified form. In this manner, antibodies specific for the antigen (the primary antibody) will specifically react with the bound antigen. Thereafter, a secondary antibody bound to, or labeled with, a detectable moiety can be added to enhance the detection of the primary antibody. Generally, the secondary antibody or other ligand which is reactive, either specifically with a different epitope of the antigen or nonspecifically with the ligand or reacted antibody, will be selected for its ability to react with multiple sites on the primary antibody. Thus, for example, several molecules of the secondary antibody can react with each primary antibody, making the primary antibody more detectable.
   Detectable Moieties
   The detectable moiety will allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy), alkaline phosphatase (for biochemical detection by color change) and radioisotopes (for radiography). The detection methods and moieties used can be selected, for example, from the list above or other suitable examples by the standard criteria applied to such selections (46).
Detecting Disease or Predisposition to Disease
   Peptic Ulceration
   Because the purified TagA antigen provided herein is associated with peptic ulceration, the present invention also provides a method of determining predisposition to peptic ulceration in a subject. The method can be accomplished according to the methods set forth above for the detection of *H. pylori* expressing the TagA antigen or for the detection of antibodies specific to the TagA antigen or for the detection of specific antibodies to the TagA antigen. The presence of the TagA antigen or TagA specific antibodies indicates a predisposition of the subject to peptic ulceration. The methods described below for detecting nucleic acids specific for tagA$^+$ strains can also be used.
   Gastric Carcinoma
   Because the purified TagA protein provided herein is associated with gastric cancer, the present invention also provides a method of determining predisposition to gastric carcinoma in a subject. The method can be accomplished according to the methods set forth above for the detection of tagA⁺ *H. pylori* strains or for the detection of antibodies specific to the TagA antigen or for the detection of specific antibodies to the TagA antigen. The presence of the TagA antigen or TagA specific antibodies indicates a predisposition of the subject to gastric carcinoma. Example 4 provides supporting human data and an example of a specific protocol for practicing this method. The methods described below for detecting nucleic acids specific for tagA⁺ strains can also be used.

Treatment Methods

Methods of treating peptic ulcers in a subject using the compositions of the present invention are provided. For example, in one such method an amount of ligand (e.g., antibody or antibody fragment) specifically reactive with the approximately 120–128 kDa antigen of *H. pylori* sufficient to bind the antigen in the subject and improve the subject's clinical condition is administered to the subject. Such improvement results from the ligand interfering with the antigen's normal function in inducing inflammation and cellular damage. The ligand can be a purified monoclonal antibody specifically reactive with the antigen, a purified polyclonal antibody derived from a nonhuman animal, or other reagent having specific reactivity with the antigen. Additionally, cytotoxic moieties can be conjugated to the ligand/antibody by standard methods. Examples of cytotoxic moieties include ricin A chain, diphtheria toxin and radioactive isotopes.

Another method of treating peptic ulcers in a subject comprises administering to the subject an amount of a ligand/antagonist for a receptor for the 120–128 kDa antigen of *H. pylori* sufficient to react with the receptor and prevent the binding of the 120–128 kDa antigen to the receptor. An antagonist for the receptor is thus contemplated. The result is an improvement in the subject's clinical condition. Alternatively, the treatment method can include administering to the subject an amount of an analogue of a TagA receptor to result in competitive binding of the TagA antigen, thus inhibiting binding of the TagA antigen to its wild type receptor. The receptor is localized on cells present in the gastroduodenal mucosa, such as epithelial cells, inflammatory cells, or endothelial cells.

Because the expression of TagA is shown to be associated with gastric carcinoma, the above treatment methods are applicable to the treatment or prevention of gastric carcinoma.

Mutant Organism

The present invention also provides a mutant *H. pylori* in which the tagA gene product has been rendered nonfunctional. The mutant can either not express tagA or express a non-functioning TagA antigen. In one example, the mutant *H. pylori* strain is obtained by making a substitution mutation in the coding sequence for the TagA antigen as described in Example 2. Since the present invention provides the nucleic acid encoding the antigen, other methods of mutating the coding sequence of the antigen can be used to obtain other mutant strains as contemplated herein. An example of the mutant *H. pylori* strain of the present invention is designated 84–183:M22 and is deposited with the American Type Culture Collection (1230 Parklawn Drive, Rockville, Md. 20852) under ATCC Accession Number 55359.

Additional isogenic mutants can be prepared, for example, by inserting a nucleic acid in the tagA gene or deleting a portion of the tagA gene so as to render the gene non-functional or produced in such low amounts that the organism is non-infectious. Furthermore, by providing the nucleotide sequence for the nucleic acid encoding the antigen, the present invention permits the making of specific point mutations having the desired effect. The deletion, insertion or substitution mutations can be made in the gene sequence in either the regulatory or coding region to prevent transcription or to render the transcribed product nonfunctional.

One such approach to the construction of a deletion or insertion mutant is via the Donnenberg method (47). A deletion in tagA is created by deleting a 0.2 kb BamH1-NdeI fragment and religating the tagA clone. This mutant is cloned into suicide vector pILL570. The sacB gene of *Bacillus subtilis* is also cloned into the suicide vector to provide a conditionally lethal phenotype. This construct is transformed into *H. pylori* by electroporation, and transformants selected by spectinomycin resistance. The merodiploid strain which contains the suicide vector and the mutated version of the tagA gene are exposed to sucrose to directly select for organisms that have undergone a second recombination, resulting in the loss of the vector. These and other well known methods of making mutations can be applied to the nucleic acids provided herein to obtain other desired mutations.

Non-isogenic mutants are also within the scope of the invention. For example, a live attenuated *H. pylori* that is also a tagA⁻ mutant according to the present invention, is provided. A tagA⁻recA⁻ mutant strain is constructed, for example, by insertion mutation of both the tagA and recA genes, according to the methods taught herein and taught in U.S. Ser. No. 08/215,928, now U.S. Pat. No. 5,434,253 for recA. A tagA⁻vacA⁻ mutant strain is constructed, for example, by insertion mutation of both the tagA and vacA genes, according to the methods taught herein for tagA and in U.S. application Ser. No. 08/215,928, now U.S. Pat. No. 5,434,253 which describes the generation of a vacA mutant. A recA⁻tagA⁻vacA⁻ mutant strain is constructed, for example, by insertion mutation of the recA, tagA and vacA genes, according to the methods taught herein for recA and vacA, and taught in U.S. Ser. No. 08/215,928, now U.S. Pat. No. 5,434,253. Any of the well known methods of mutating a gene can be used in the present invention to generate *H. pylori* mutant strains. The strains can be tested as provided for immunogenicity.

Vaccines

The antigen, antigenic fragment or mutant *H. pylori* of this invention can be used in the construction of a vaccine comprising an immunogenic amount of the antigen or mutant *H. pylori* and a pharmaceutically acceptable carrier. The vaccine can be the entire antigen, the antigen on an intact *H. pylori*, *E. coli* or other strain. The vaccine can then be used in a method of preventing peptic ulceration or other complications of *H. pylori* infection (including atrophic gastritis and malignant neoplasms of the stomach).

Immunogenic amounts of the antigen can be determined using standard procedures. Briefly, various concentrations of a putative specific immunoreactive epitope are prepared, administered to an animal and the immunological response (e.g., the production of antibodies) of an animal to each concentration is determined.

The pharmaceutically acceptable carrier in the vaccine of the instant invention can comprise saline or other suitable carriers (48). An adjuvant can also be a part of the carrier of the vaccine, in which case it can be selected by standard criteria based on the antigen used, the mode of administration and the subject (48). Methods of administration can be by oral or sublingual means, or by injection, depending on the particular vaccine used and the subject to whom it is administered.

It can be appreciated from the above that the vaccine can be used as a prophylactic or a therapeutic modality. Thus, the invention provides methods of preventing or treating H. pylori infection and the associated diseases by administering the vaccine to a subject.

Nucleic Acid Detection (Diagnosis) Methods

The presence of the TagA antigen and H. pylori possessing the TagA antigen can also be determined by detecting the presence of a nucleic acid specific for the antigen. The specificity of these sequences for the antigen can be determined by conducting a computerized comparison with known sequences, catalogued in GenBank, a computerized database, using the computer programs Word Search or FASTA of the Genetics Computer Group (Madison, Wis.), which search the catalogued nucleotide sequences for similarities to the gene in question.

The nucleic acid specific for the antigen can be detected utilizing a nucleic acid amplification technique, such as polymerase chain reaction or ligase chain reaction. Alternatively, the nucleic acid is detected utilizing direct hybridization or by utilizing a restriction fragment length polymorphism. For example, the present invention provides a method of detecting the presence of H. pylori, possessing the TagA antigen, comprising ascertaining the presence of a nucleotide sequence associated with a restriction endonuclease cleavage site. In addition, PCR primers which hybridize only with nucleic acids specific for the antigen can be utilized. The presence of amplification indicates the presence of the antigen. In another embodiment a restriction fragment of a DNA sample can be sequenced directly using, for example, Sanger ddNTp sequencing or 7-deaza-2'-deoxyguanosine 5'-triphosphate and Taq polymerase and compared to the known unique sequence to detect H. pylori. In a further embodiment, the present invention provides a method of detecting the presence of tagA-containing H. pylori by selective amplification by the methods described above. In yet another embodiment H. pylori can be detected by directly hybridizing the unique sequence with a tagA specific nucleic acid probe. Furthermore, the nucleotide sequence could be amplified prior to hybridization by the methods described above.

Once specific variable sequences are shown to be associated with peptic ulceration, the methods to detect these sequences are standard in the art. Detection of point mutations or variable sequences using direct probing involves the use of oligonucleotide probes which may be prepared, for example, synthetically or by nick translation. The probes may be suitably labeled using, for example, a radio label, enzyme label, fluorescent label, biotin-avidin label and the like for subsequent visualization in the example of Southern blot hybridization procedure. The labeled probe is reacted with a bound sample DNA, e.g., to a nitrocellulose sheet under conditions such that only fully complementary sequences hybridize. The areas that carry DNA sequences complementary to the labeled DNA probe become labeled themselves as a consequence of the reannealing reaction. The areas of the filter that exhibit such labeling may then be visualized, for example, by autoradiography. The labeled probe is reacted with a DNA sample bound to, for example, nitrocellulose under conditions such that only fully complementary sequences will hybridize. The stringency of hybridization is usually 5° C. below the Ti (the irreversible melting temperature of the hybrid formed between the probe and its target sequence) for the given chain length. For 20mers the recommended hybridization temperature is about 58° C. The washing temperatures are unique to the sequence under investigation and need to be optimized for each variant.

Alternative probing techniques, such as ligase chain reaction (LCR), involve the use of mismatch probes, i.e., probes which are fully complementary with the target except at the point of the mutation. The target sequence is then allowed to hybridize both with oligonucleotides which are fully complementary and have oligonucleotides containing a mismatch, under conditions which will distinguish between the two. By manipulating the reaction conditions, it is possible to obtain hybridization only where there is full complementarity. If a mismatch is present there is significantly reduced hybridization.

The polymerase chain reaction (PCR) is a technique that amplifies specific DNA sequences with remarkable efficiency. Repeated cycles of denaturation, primer annealing and extension carried out with polymerase, e.g., a heat stable enzyme Taq polymerase, leads to exponential increases in the concentration of desired DNA sequences. Given a knowledge of the nucleotide sequence of a mutation, synthetic oligonucleotides can be prepared which are complementary to sequences which flank the DNA of interest. Each oligonucleotide is complementary to one of the two strands. The DNA can be denatured at high temperatures (e.g., 95° C.) and then reannealed in the presence of a large molar excess of oligonucleotides. The oligonucleotides, oriented with their 3' ends pointing towards each other, hybridize to opposite strands of the target sequence and prime enzymatic extension along the nucleic acid template in the presence of the four deoxyribonucleotide triphosphates. The end product is then denatured again for another cycle. After this three-step cycle has been repeated several times, amplification of a DNA segment by more than one million-fold can be achieved. The resulting DNA may then be directly sequenced in order to locate any genetic alteration. Alternatively, it may be possible to prepare oligonucleotides that will only bind to altered DNA, so that PCR will only result in multiplication of the DNA if a mutation is present. Following PCR, direct visualization or allele-specific oligonucleotide hybridization may be used to detect disease associated with a point mutation. Alternatively, an adaptation of PCR called amplification of specific alleles (PASA) can be employed; this uses differential amplification for rapid and reliable distinction between alleles that differ at a single base pair. Other techniques, such as 3SR, which utilize RNA polymerase to achieve high copy number, can also be used where appropriate.

In yet another method, PCR may be followed by restriction endonuclease digestion with subsequent analysis of the resultant products. Nucleotide substitutions can result in the gain or loss of specific restriction endonuclease site. The gain or loss of a restriction endonuclease recognition site facilitates the detection of the disease associated mutation using restriction fragment length polymorphism (RFLP) analysis or by detection of the presence or absence of a polymorphic restriction endonuclease site in a PCR product that spans the sequence of interest.

For RFLP analysis, DNA is obtained, for example from the blood, gastric specimen, saliva, dental plaque, other bodily fluids or stool of the subject suspected of containing tagA-possessing H. pylori, or H. pylori isolated from subject, and from a subject infected with nontoxic H. pylori, is digested with a restriction endonuclease, and subsequently separated on the basis of size by agarose gel electrophoresis. The Southern blot technique can then be used to detect, by hybridization with labeled probes, the products of endonuclease digestion. The patterns obtained from the Southern blot can then be compared. Using such an approach, tagA DNA is detected by determining the number of bands detected and comparing this number to the DNA from *H. pylori* strains that are not associated with severe disease. Restriction endonucleases can also be utilized effectively to detect mutations in the tagA gene.

Similar creation of additional restriction sites by nucleotide substitutions at the disclosed mutation sites can be readily calculated by reference to the genetic code and a list of nucleotide sequences recognized by restriction endonucleases.

Single strand conformational analysis (SSCA) offers a relatively quick method of detecting sequence changes which may be appropriate in at least some instances.

In general, primers for PCR and LCR are usually about 20 bp in length and the preferable range is from 15–25 bp. Better amplification is obtained when both primers are the same length and with roughly the same nucleotide composition. PCR conditions can include denaturation of strands usually takes place at 94° C. and extension from the primers is usually at 72° C. The annealing temperature varies according to the sequence under investigation. Examples of reaction times are: 20 mins denaturing; 35 cycles of 2 min, 1 min, 1 min for annealing, extension and denaturation; and finally a 5 min extension step.

PCR amplification of specific alleles (PASA) is a rapid method of detecting single-base mutations or polymorphisms. PASA (also known as allele specific amplification) involves amplification with two oligonucleotide primers such that one is allele-specific. The desired allele is efficiently amplified, while the other allele(s) is poorly amplified because it mismatches with a base at or near the 3' end of the allele-specific primer. Thus, PASA or the related method of PAMSA may be used to specifically amplify the mutation sequences of the invention. Where such amplification is done on *H. pylori* isolates or samples obtained from an individual, it can serve as a method of detecting the presence of the mutations.

As mentioned above, a method known as ligase chain reaction (LCR) can be used to successfully detect a single-base substitution. LCR probes may be combined or multiplexed for simultaneously screening for multiple different mutations. Thus, LCR can be particularly useful where, as here, multiple mutations are predictive of the same disease.

Antigen-Detecting Kit

The present invention provides a kit for the diagnosis of infection by strains of *H. pylori* possessing the TagA antigen. Particularly, the kit can detect the presence of TagA antigen specifically reactive with an antibody or an immunoreactive fragment thereof. The kit can include an antibody bound to a substrate, a secondary antibody reactive with the antigen and a reagent for detecting binding of the secondary antibody to the antigen. Such a kit can be an ELISA kit and can comprise the substrate, primary and secondary antibodies when appropriate, and any other necessary reagents such as detectable moieties, enzyme substrates and color reagents as described above. The diagnostic kit can, alternatively, be an immunoblot kit generally comprising the components and reagents described herein.

Antibody-Detecting Kit

The diagnostic kit of the present invention can be used to detect the presence of a primary antibody specifically reactive with TagA or an antigenic fragment thereof. The kit can include the antigen bound to a substrate, a secondary antibody reactive with the antibody specifically reactive with the TagA antigen and a reagent for detecting binding of the secondary antibody to the primary antibody. Such a kit can be an ELISA kit and can comprise the substrate, antigen, primary and secondary antibodies when appropriate, and any other necessary reagents such as detectable moieties, enzyme substrates and color reagents as described above. The diagnostic kit can, alternatively, be an immunoblot kit generally comprising the components and reagents described herein.

Nucleic Acid Detection (Diagnostic) Kits

Once the nucleotide sequence of the TagA antigen is determined, the diagnostic kit of the present invention can alternatively be constructed to detect nucleotide sequences specific for the antigen comprising the standard kit components such as the substrate and reagents for the detection of nucleic acids. Because *H. pylori* infection can be diagnosed by detecting nucleic acids specific for the antigen in gastric or duodenal tissue and body fluids such as gastric juice, urine, stool, and saliva, it will be apparent to an artisan that a kit can be constructed that utilizes the nucleic acid detection methods, such as specific nucleic acid probes, primers or restriction fragment length polymorphisms in analyses. It is contemplated that the diagnostic kits will further comprise a positive and negative control test.

The particular reagents and other components included in the diagnostic kits of the present invention can be selected from those available in the art in accord with the specific diagnostic method practiced in the kit. Such kits can be used to detect the antigen in tissue and fluid samples from a subject.

The following examples are intended to illustrate, but not limit, the invention. While they are typical of those that might be used, other procedures known to those skilled in the art may be alternatively employed.

EXAMPLE 1

Cloning and Expression of TagA Antigen

Bacterial strains and growth conditions

*H. pylori* strain 84–183 (ATCC 53726) was used to clone the gene for the TagA antigen. Thirty-two clinical *H. pylori* isolates from humans, including strains that had been previously shown to possess the antigen, were used to assess conservation of the gene and correlation with cytotoxin production (Table 1). Stock cultures were maintained at −70° C. in Brucella broth (BBL Microbiology Systems, Cockeysville, Md.) supplemented with 15% glycerol. *H. pylori* strains were cultured in Brucella broth supplemented with 5% fetal bovine serum in a microaerobic atmosphere (generated by CampyPak-Plus (BBL) at 37° C. for 48 hours. For transformation and protein expression, *E. coli* strains XL1-Blue (Stratagene, La Jolla, Calif.), HB101 (ATCC 33694), and DH5α (Stratagene, La Jolla, Calif.) were cultured in Luria-Bertoli (LB) medium with shaking at 37° C. The final concentrations of ampicillin when, added to media was 100 μg/ml.

Chemicals and enzymes

Isopropyl-β-D-thiogalactopyranoside (IPTG) was purchased from Sigma Chemical Co. (St. Louis, Mo.) and used at 57 μg/ml, and 5-bromo-4-chloro-3-indolyl-β-D-galactoside (X-GAL; final concentration 40 μg/ml) was from Boehringer-Mannheim (Indianapolis, Ind.). Restriction enzymes, T4 DNA ligase, *E. coli* DNA polymerase large (Klenow) fragment and Sequenase™ were from Promega and United States Biochemicals (Cleveland, Ohio). [α-$^{32}$p] dATP (650 Ci/mmol) was from ICN Radiochemicals (Irvine, Calif.).

Genetic techniques and nucleotide sequence analysis

To obtain chromosomal DNA from *H. pylori* 84–183, the strain was cultured for 48 h in Brucella broth containing 5% fetal bovine serum, the cells pelleted, and resuspended in 100 mM Tris-HCl (pH 7.2) containing 100 mM NaCl. Cells were lysed using 1% SDS in 100 mM Tris-HCl (pH 8.8). After chloroform-phenol extractions, the chromosomal DNA was precipitated with 100% ethanol. Plasmids were isolated by the rapid alkaline extraction procedure of Birnboim and Doly (49) and purification was completed by precipitation in the presence of 800 mM NaCl and 6.5% polyethylene glycol. All other standard molecular genetic techniques, including sequential ordered deletions, were performed as described (50). The nucleotide sequence was determined unambiguously on both strands using double-stranded DNA templates and the dideoxy chain termination procedure as described previously (51). Oligonucleotide primers were synthesized by the Vanderbilt University DNA Core Facility using a Milligen 7500 DNA synthesizer, using the manufacturer's protocol. Nucleotide sequences were compiled and analyzed with the aid of the DNA-Star program (DNA Star, Inc., Madison, Wis.); putative promoter and Shine-Dalgarno sequences were identified by comparison with consensus sequences (52).

Construction of a genomic library from *H. pylori*

Strain 84–183 chromosomal DNA was sheared by sonication and the resulting fragments were electrophoresed on a 0.7% low melting temperature agarose gel. Fragments in the 2–10 kb size range were excised, treated with T4 DNA polymerase to produce blunt ends, and ligated to phosphorylated EcoRI octamer linkers (New England Biolabs, Beverly, Mass.). The DNA was digested with EcoRI and ligated to the EcoRI arms of the λZapII vector, according to the manufacturer's protocol. The ligation mixtures were added to the Gigapack IIa packaging mix (Stratagene) and titered on XL1-blue cells (lambda ZapII) or Y1088 (lambda gt11) cells. The amplified phage libraries were screened with adsorbed sera from an *H. pylori*-infected person or by plaque hybridization.

Cloning of *H. pylori*-specific genes

Serum from an *H. pylori*-infected person that strongly recognizes the 120–128 kDa antigen was adsorbed with *H. pylori* strain 86–313, which does not produce the 120–128 kDa band, and with *E. coli* cells to reduce the likelihood of nonspecific reactivity and then used to screen a bank of genes from the amplified λZapII phage library (53). The bank contained approximately $4 \times 10^4$ insertions. The amplified phage library was screened by allowing approximately $10^5$ plaques to grow on XL1 Blue cells for 2.5 h at 42° C., overlaying with a nitrocellulose filter previously impregnated with 10 mM IPTG, and incubating for 2 h at 37° C. The filters were then screened with the adsorbed serum to detect 9 reactive clones. Positive plaques were then plaque purified, and lysates were prepared from these infected *E. coli* cells. The lysates were immunoblotted with the adsorbed serum and clones expressing recombinant proteins were saved. By immunoblotting with the adsorbed human serum, each of the XL1-Blue lysates showed a strongly immunoreactive band migrating at either approximately 75, 85, or 96 kDa, corresponding to plasmids pMC1, pMC2, or pMC3, respectively.

From the three representative clones, the pBluescript plasmids containing the cloned DNA inserts were excised by co-infection with helper phage, as detailed (54), and fresh XL1-Blue cells transformed. After plasmid purification, restriction enzyme cleavage maps were generated and the plasmids used for further characterization. In a parallel study, four clones were isolated from a λgt11 library of *H. pylori* 84–183 DNA by the same methodology, and the DNA insert from one of four positive clones was amplified by polymerase chain reaction (PCR) using primers based on the known flanking λgt11 sequences. Recombinant phage DNA from four positive plaques was purified, and each contained a 0.6 kb insert. Immunoblot analysis of lysates from two clones (λYB1 and λYB2) showed similar sized 130 kDa bands that reacted with the adsorbed human antiserum. To determine whether the 130 kDa protein was synthesized by a recombinant phage as a fusion protein, cell lysate prepared from λYB1 was subjected to immunoblot analysis using β-galactosidase specific antiserum. The cross-reactivity shown indicates that the recombinant clone XYB1 contains a fusion of the λgt11 β-galactosidase large (116 kDa) fragment and an *H. pylori* open reading frame. We cloned the λYB1 insert into pUC19, but the recombinant (pYB1) did not express any protein.

Gel electrophoresis and immunoblot analysis

Lysates from *E. coli* carrying recombinant lambda gt11, λZapII or pBluescript were analyzed by SDS-PAGE and immunoblotting with adsorbed human serum. Discontinuous sodium dodecyl sulfate (SDS)-poly-acrylamide gel electrophoresis (PAGE) was performed as described previously (55) by using a 4.5% stacking gel and a 7.0% separating gel. Samples containing 3 μg of protein were applied to each gel lane. After electrophoresis, gels were fixed and proteins were resolved by the modified silver stain method of Oakley et al. (56). Concentrated culture supernatants containing protein were diluted in sample buffer and were layered onto the surface of a polyacrylamide gel in a Mini-PROTEAN II slab cell (Bio-Rad Laboratories, Richmond, Calif.). Following electrophoresis, proteins were transferred to nitrocellulose paper by electro blotting for 1 h at 1 amp. After nonspecific binding was blocked, the nitrocellulose paper was incubated at room temperature for 1 h with 1:100 dilutions of serum samples. Alkaline-phosphatase conjugates of goat anti-human IgG, (Tago, Inc., Burlingame, Calif.), in a dilution of 1:2,000 were used as the second antibody.

Southern hybridization

*H. pylori* or *C. jejuni* chromosomal DNA was digested with either HindIII or EcoRI and BamHI and the resulting fragments were electrophoresed on a 0.7% agarose gel in 0.04M Tris-acetate –2 mM EDTA buffer (pH 8.2). All hybridization conditions and procedures were exactly as described (50). Probes were radiolabeled by primer extension using random hexamers (57). Hybridization was carried out at 68° C. for 16 h in buffer containing 6× SSC (1× SSC is 0.15M NaCl, 0.015M sodium citrate), 0.5% sodium dodecyl sulfate (SDS), 5× Denhardt's solution (1× Denhardt's solution is 0.02% Ficoll, 0.02% polyvinylpyrrolidone, 0.02% bovine serum albumin), and 100 μg/ml salmon sperm DNA. The blots were washed at 60° C. in 0.5× SSC and exposed to XAR-2 X-ray film (Eastman Kodak, Rochester, N.Y.).

Colony hybridization

*H. pylori* strains were grown on trypticase soy blood agar plates (BBL) and replica copies of these colonies were transferred to nitrocellulose filters. Each filter was placed on 3 mm Whatman paper saturated with 0.2M NaOH/1.5M NaCl. After 3 min the filter was transferred to 3 mm Whatman paper saturated with 0.4M Tris-Cl (pH 7.6)/2× SSC for 3 min, and then to 2× SSC for 3 min. The colony blot filters were dried in a vacuum oven for 90 min at 80° C. and hybridized with radiolabeled pMC3 as described (50).

Cytotoxin production

*H. pylori* broth culture supernatants were concentrated 30-fold by ultrafiltration, passaged through a 0.2 μM filter, and incubated with HeLa cells. Briefly, *H. pylori* strains were cultured at 37° C. in brucella broth (BBL, Microbiology Systems, Cockeysville, Md.) containing 5% defined fetal bovine serum (Hyclone, Logan, Utah), supplemented with 10 mM ammonium chloride to potentiate cytotoxin activity. Broth cultures were incubated in a microaerobic atmosphere on a gyratory shaker at 100 rpm for 72 h. Cultures were centrifuged at 3,000×g for 15 min, and the cell-free supernatants were stored at −70° C. After thawing, supernatants were concentrated 30-fold by using a 30-kDa ultrafiltration membrane, and retentates were sterilized by passage through a 0.22-μm-pore-size filter. These concentrated culture supernatants (CCS,) were incubated with HeLa cells (obtained from Allison O'Brien, Uniformed Services University of the Health Sciences, Bethesda, Md.) in twofold dilutions from 1:10 to 1:320 as described previously (39), except that toxicity assays were performed in a total volume of 100 μl in 96-well well microtiter plates (Falcon; Becton Dickinson and Co., Lincoln Park, N.J.).

Vacuolation of HeLa cells was quantitated using a neutral red uptake assay. Briefly, a stock solution of 0.5% purified grade neutral red (Sigma Chemical Co., St. Louis, Mo.) was prepared in 0.9% saline and filtered with Whatman no. 1 filter pater. Staining solutions were prepared before each experiment by diluting the stock solution 1:10 in Eagle medium containing 10% fetal bovine serum. After incubation with test samples for 24 h the medium overlaying HeLa cells was removed and replaced with 100 μl of staining solution per well for 4 min. The cells were washed twice with 150 μl of 0.9% saline per well, and the neutral red was extracted from cells by the addition of 100 μl of acidified alcohol per well (58). The optical density (OD) at 540 nm of wells was determined by using an MR700 enzyme-linked immunosorbent assay reader (Dynatech, Alexandria, Va.). All assays were performed in triplicate. In all experiments, the mean OD of wells containing cells incubated with medium alone was less than 0.130 (mean, 0.101±0.007); this background OD was subtracted from the OD of experimental wells to yield a net OD. Of the 32 $H.$ $pylori$ strains tested, 15 produced the vacuolating cytotoxin, as determined in this assay (Table 3).

Mapping the pBluescript inserts

After digestion with EcoRI, plasmids pMC1, pMC2, and pMC3 were found to contain DNA inserts of approximately 2.5, 2.7, and 3.6 kb, respectively. Analysis of restriction endonuclease treatment of the recombinant plasmids identified a conserved 1.2 kb HindIII-digestion fragment in all three (FIG. 1). As such, further studies concentrated on pMC3, which contained the largest insert. Analysis of deletion mutations produced by exonuclease III digestion, identified the orientation and approximate location of the open reading frame (ORF) (FIG. 1, large arrow).

Sequence analysis of pMC3 and pYB1

To determine the sequence of the 3.6 kb insert in pMC3, a series of nested ordered deletions of the plasmid using exonuclease III (FIG. 1) was performed, as described (50). In total, the sequence for the entire pMC3 insert representing 3648 bp was determined on both strands (SEQ ID NO:1). The nucleotides are numbered on the right of each line. The nucleotides encoding the glycine at residue number 859 of SEQ ID NO:1 are an artifact of the cloning process and are not a part of the tagA gene. SEQ ID NO:2 provides the deduced amino acid sequence of the nucleic acid shown in SEQ ID NO:1.

A long open reading frame commencing at nucleotide 1072 continues to the termination of the insert. Two other open reading frames in the opposite orientation begin at 645 bp and 264 bp. The deduced amino acids are shown beneath the nucleotides. Potential ribosomal binding-sites (Shine-Delgarno sequence; SD), and putative promoter elements (−35 and −10 sequences) are indicated. Only a single ORF exceeding 300 bases was found in any of the six possible reading frames. This ORF encodes a TagA antigen of 859 amino acids, yielding a predicted protein with a molecular weight of 96,022 (SEQ ID NO: 2). The direction of transcription deduced from this ORF is also in agreement with that determined previously by the use of the deletion mutants. However, there is no translation termination signal, indicating that the ORF in pMC3 is truncated. The truncated fragment is rich in basic amino acids (Table 2) and the predicted isoelectric point is 8.0. A potential ribosomal binding site (AGGAG) ends 6 bp upstream of the ORF. The sequence 112 bp upstream of the translational start site exhibits the promoter sequence TATAGT (SEQ ID NO: 1) which resembles the Pribnow consensus promoter sequence TATNATN (Hawley and McClure). This putative −10 region, which is similar to a sigma-70 promoter, is associated with a −35 region, ATGCCA, which shares 4 of 6 bases with the corresponding consensus sequence, TTGACA (52). The deduced amino acid composition of the truncated polypeptide is shown in Table 2.

Two smaller ORFs, each proceeding in the opposite direction, also were identified (SEQ ID NO: 1). The first, encoding a polypeptide of 79 amino acids, commences at bp 645 and is not proceeded by an obvious Shine Delgarno or putative promoter sequence. The second ORF commences at bp 264 and encodes 88 amino acids before the end of the insert. This truncated ORF is preceded by a Shine Dalgarno sequence, and the sequence TTTGAT 90 bp upstream of the translational start site resembles the −10 consensus promoter site, followed by the sequence TTGTCA, which shares 5 of 6 bases with the −35 consensus sequence (52).

The 0.6 kb insert in pYB1 was sequenced using both forward and reverse primers of the known λgt11 flanking sequences along with additional primers based on experimentally-derived insert sequences. The first 464 bases of the 620 bp pYB1 sequence overlapped with the end of pMC3, but the ORF still continued.

Serologic recognition of the truncated recombinant TagA antigen

In addition to the index case, sera from $H.$ $pylori$-infected persons that recognize the TagA antigen from $H.$ $pylori$ strain 84–183 recognize the recombinant polypeptide. For this analysis, we studied serum from 6 persons not infected with $H.$ $pylori$, and from 14 infected persons (7 did and 7 did not recognize the 120–128 kDa antigen from strain 84–183). Using lysates of $E.$ $coli$ XL1-Blue transformed with pMC3 and immunoblotting, there is clear recognition of the 96 kDa antigen by human serum IgG. In total, 4 of 7 sera that recognize the native 120–128 kDa band also strongly recognize the recombinant protein versus none of the 13 sera tested that do not recognize the 120–128 kDa band (p=0.007, Fisher's exact test, 2-tailed). If weak reactions to the pMC3 band are considered, then all 7 sera that recognize the 120–128 kDa band, and 3 of 13 of the non-recognizing sera react to the recombinant protein (p=0.003, Fisher's exact test, 2-tailed). Thus, the recombinant protein produced by pMC3 can be used for serologic assays to detect antibodies to the $H.$ $pylori$ 120–128 kDa antigen.

Conservation of the tagA gene

To determine whether other $H.$ $pylori$ strains possess the tagA gene or homologous sequences, 32 strains were studied by colony hybridization using pMC3 as a probe (Table 3). A positive signal was obtained from 19 (59.3%) of these strains. SDS-PAGE and immunoblotting of whole cells of these strains indicated that 19 (59.3%) of the 32 strains expressed a band at 120–128 kDa. The immunoblot and colony hybridization findings correlated completely; all 19 H. pylori strains expressing the protein possessed a gene homolog, in comparison to none of the 13 strains not expressing the protein (p<0.001, Fisher's exact test, one-tailed). In addition, all 15 strains producing the vacuolating cytotoxin showed both pMC3 hybridization and presence of the 120–128 kDa band (Table 3).

To gain information on the restriction fragment polymorphism of the tagA gene and whether there are multiple homologous genes in each bacterial genome, genomic DNA from 4 H. pylori strains was prepared and Southern hybridization performed using pMC3 as the probe. Two strains expressing the 120–128 kDa protein and with positive colony hybridization now showed strong hybridization to a HindIII restriction fragment migrating at approximately 1.2 kb, and weaker bands at 3.0 and 3.3 kb. For a third strain that showed the phenotype and had a positive colony hybridization, the probe hybridized strongly in the Southern analysis to a band of about 1.1 kb; no weaker bands were seen. A band migrating at less than 0.5 kb that hybridized weakly with the probe was present in all three strains. An H. pylori strain that expressed no 120–128 kDa protein and that had a negative colony hybridization, as well as a C. jejuni strain used as a control, showed lack of hybridization in the Southern analysis. Hybridization of pMC3 to chromosomal DNA from strains 84–183 and 60190 digested with EcoRI and BamHI also showed polymorphism, confirming the heterogeneity observed with the other restriction enzyme. These studies indicate that although homologs of TagA exist in other H. pylori strains, there is heterogeneity in either intragenic or flanking sequences.

The present example provides a cloned fragment of H. pylori genomic DNA that includes the majority of a gene that encodes an important H. pylori antigen. The evidence that pMC3 contains the gene encoding the TagA antigen may be summarized as follows: (i) neither the protein nor the gene are present in all H. pylori strains; (ii) only strains expressing the 120–128 kDa protein hybridize with pMC3 and strains that do not express the protein do not hybridize; (iii) sera from H. pylori-infected persons that recognize the 120–128 kDa antigen recognize the product of recombinant tagA significantly more frequently than do control sera.

The partial sequences of tagA and the two other ORFs have no identity with the N-terminus or 3 internal sequences from the 87 kDa cytotoxin. This finding is consistent with earlier observations that the 120–128 kDa and 87 kDa proteins are antigenically unrelated (41). Comparison of the truncated deduced gene product revealed little direct homology with known proteins.

The tagA gene or homologous genes are present in approximately 60% of the H. pylori isolates studied but absent from the others. As indicated by the Southern analysis, there is evidence for restriction fragment polymorphism even when only a small number of strains are examined. Absence of a homolog correlated exactly with lack of expression of an antigenic band at 120–128 kDa. Thus, the phenotype lacking this band is not due to deficiencies related to transcription or expression but rather to the absence of the implicated gene.

The presence of genomic DNA containing at least the truncated tagA gene is highly associated with cytotoxin production. A minority of strains that possess the tagA gene do not produce detectable levels of cytotoxin. This phenomenon may reflect suboptimal sensitivity in the cell culture assay to detect toxin, or may indicate that factors other than the TagA antigen are associated with toxin activity.

As shown by the immunoblot studies, the pMC3 products are excellent diagnostic reagents for detection of human serum antibodies to the TagA antigen. Use of this recombinant protein can readily supply sufficient antigen to aid in development of immunoassays to determine which persons are infected with H. pylori strains producing the native 120–128 kDa protein, and heterologous antibodies raised against the pMC3 gene product can be used to determine which strains produce the TagA antigen. Knowledge of the DNA sequence of pMC3 permits the construction of oligonucleotides for use as hybridization probes or for primers for PCR. Such techniques are also used for rapid detection of infection due to a strain with the implicated genotype. Creation of deletion mutants enables elucidation of the role of this gene product and provides both therapeutic reagents and vaccine candidates. Such diagnostic methods and mutants are detailed herein.

TABLE 1

Helicobacter pylori strains used in this study

| Strain designation | Isolation locale | Expression of 120–128 kDa antigen[a] | Expression of vacuolating cytotoxin activity[b] |
|---|---|---|---|
| Tx30a | Texas | − | − |
| 84–183 | Texas | + | + |
| 60190 | England | + | + |
| 87–29 | Colorado | + | + |
| 86–313 | Colorado | − | − |
| 87–199 | Colorado | + | + |
| 86–385 | Colorado | − | − |
| 87–33 | Colorado | + | + |
| 87–81 | Colorado | + | + |
| 87–91 | Colorado | + | + |
| 87–90 | Colorado | − | − |
| 87–226 | Colorado | + | − |
| 87–225 | Colorado | − | − |
| 87–230 | Colorado | − | − |
| 87–75 | Colorado | − | − |
| 87–203 | Colorado | − | − |
| 87–6 | Colorado | + | − |
| 86–338 | Colorado | − | − |
| 86–63 | New York | + | − |
| 86–86 | New York | + | + |
| 86–332 | Minnesota | + | + |
| 92–18 | Tennessee | + | + |
| 92–19 | Tennessee | + | + |
| 92–20 | Tennessee | − | − |
| 92–21 | Tennessee | + | + |
| 92–22 | Tennessee | + | − |
| 92–23 | Tennessee | − | − |
| 92–24 | Tennessee | − | − |
| 92–25 | Tennessee | + | + |
| 92–26 | Tennessee | + | + |
| 92–27 | Tennessee | + | + |
| 92–28 | Tennessee | − | − |

[a]Recognition of 120–128 kDa band in cell lysates by human serum as detected by immunoblot (20).
[b]Production of vacuolating cytotoxin as detected in HeLa cell culture (59).

TABLE 2

Amino acid composition of truncated 859 amino acid TagA polypeptide as deduced from pMC3

| Amino acid | Number of residues | Percent of 859 amino acids |
|---|---|---|
| Ala | 60 | 7.0 |
| Cys | 2 | 0.2 |
| Asp | 62 | 7.2 |
| Asn | 82 | 9.5 |
| Glu | 59 | 6.9 |
| Gln | 48 | 5.6 |
| Phe | 44 | 5.1 |

TABLE 2-continued

Amino acid composition of truncated 859 amino acid TagA polypeptide as deduced from pMC3

| Amino acid | Number of residues | Percent of 859 amino acids |
|---|---|---|
| Gly | 54 | 6.3 |
| His | 12 | 1.4 |
| Ile | 50 | 5.8 |
| Lys | 101 | 11.8 |
| Leu | 67 | 7.8 |
| Met | 12 | 1.4 |
| Pro | 24 | 2.8 |
| Arg | 22 | 2.6 |
| Ser | 63 | 7.3 |
| Thr | 30 | 3.5 |
| Val | 47 | 5.5 |
| Trp | 4 | 0.4 |
| Tyr | 16 | 1.9 |

TABLE 3

Correlation between presence of 120–128 kDa band by immunoblot, hybridization with pMC3, and cytotoxin production by 32 H. pylori isolates from humans Strain characteristics

| Presence of 120–128 kDa band on immunoblot[a] | Hybridization of pMC3 to H. pylori colony[b] | Cytotoxin production in cell culture assay[c] | Number of strains |
|---|---|---|---|
| + | + | + | 15 |
| − | − | − | 13 |
| + | + | − | 4 |
| − | − | + | 0 |
| − | + | − | 0 |
| + | − | − | 0 |
| + | − | + | 0 |
| − | + | + | 0 |

[a]Recognition of 120–128 kDa band in cell lysates by human serum as detected by immunoblot (20).
[b]Hybridization of pMC3 to lysed H. pylori cells in colony blot (50).
[c]Production of vacuolating cytotoxin as detected in HeLa cell culture (59).

EXAMPLE 2

Construction and characterization of a tagA-negative strain of Helicobacter pylori Bacterial strains, vectors and growth conditions H. pylori strain 84–183 (ATCC 53726) used in this study was from the culture collection of the Vanderbilt University Campylobacter/Helicobacter Laboratory and was chosen because it has been extensively characterized. Stock cultures were maintained at −70° C. in Brucella broth (BBL Microbiology Systems, Cockeysville, Md.) supplemented with 15% glycerol. H. pylori strains were grown in Brucella broth supplemented with 5% fetal bovine serum or on blood agar plates supplemented with nalidixic acid (50 mg/liter), vancomycin (10 mg/liter), polymyxin B (5000 U/liter), and trimethoprim (5 mg/liter) under microaerobic conditions at 37° C. for 48 hours. E. coli strain DH5α (Stratagene, La Jolla, Calif.) used for transformation, was grown in LB medium. As described above, pMC3 contains the truncated tagA gene on a 3.5 kb insert in pBluescript. Plasmid pILL600 (60) was used as a source of a C. coli kanamycin (km) resistance gene.

Chemicals and enzymes

Final concentrations of ampicillin (100 μg/ml) and kanamycin (50 μg/ml) were used whenever necessary. Restriction enzymes, T4 DNA ligase, E. coli DNA polymerase large (Klenow) fragment were from Promega and United States Biochemicals (Cleveland, Ohio). $\alpha$-$^{32}$P-dATP (650 Ci/mmol) was from ICN Radiochemicals (Irvine, Calif.).

Genetic techniques

Chromosomal DNA was prepared as described above. Plasmids were isolated by the procedure of Birnboim and Doly (49). All other standard molecular genetic techniques were performed as described (50). DNA fragments used as probes for hybridization experiments were gel-purified.

Introduction of km cassette into H. pylori strain 84–183

Figure 2:
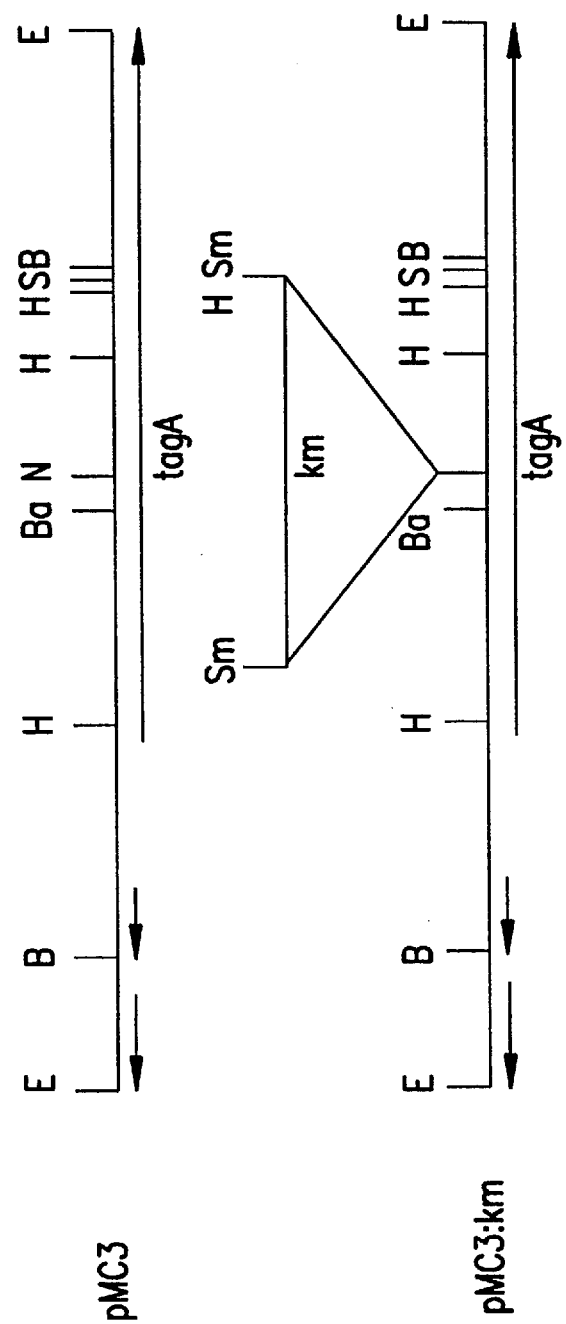
FIG. 2 shows a restriction map of pMC3:km used in construction of H. pylori mutant. The km cassette from pILL600 was ligated into the NdeI site of pMC3 to create pMC3:km. The arrows represent open reading frames including the truncated 2577 bp tagA open reading frame. Restriction sites are E, EcoRI; B, BglII; H, HindIII; Ba, BamHI; N, NdeI; S, SacI; Sm, SmaI. pMC4 represents the 2.9 kb EcoRI to SacI fragment of pMC3.

An E. coli kanamycin-resistance gene was inserted into the unique NdeI site of pMC3 to create pMC3: km (FIG. 2). This construct was introduced directly into H. pylori strain 84–183 by electroporation. Briefly, H. pylori cells grown on blood agar plates for 48 h were harvested, washed three times in electroporation buffer (15% glycerol/5% sucrose) and suspended in 200 μl of the buffer. Plasmid DNA from pMC3:km was isolated by a rapid (mini-prep) alkaline-lysis method of Birnboim and Doly and was added to the cells and incubated for 5 min on ice. The cells and DNA were transferred to 0.2 cm electroporation cuvette in a Genepulsar apparatus (Bio-Rad), and high voltage pulses (25F, 2.5 kv and 200 Ω) were delivered as described previously (61). Following electroporation, the cells were suspended in 400 μl of LB media and spread on blood agar plates. The plates were incubated at 37° C. under microaerobic conditions for 24 h, then cells were harvested, plated on blood agar plates containing 50 pg/ml of kanamycin, and incubated microaerobically for 48 h.

The cloning vector used was unable to replicate in H. pylori and selection on kanamycin-containing media yielded kanamycin-resistant recombinants. From approximately $10^{10}$ H. pylori cfu, 3000 transformants ($10^{-7}$) were obtained when 500 ng of plasmid DNA was used.

Colony hybridization

Fifty kanamycin-resistant transformants obtained by electroporation were grown on blood agar plates and replica copies of these colonies were transferred to nitrocellulose filters. Each filter was placed on 3 mM Whatman paper saturated with 0.2M NaOH/1.5M NaCl. After 3 min the filter was transferred to 3 mM Whatman paper, saturated with 0.4M Tris-HCl (pH 7.6)/2× SSC for 3 min, and then to 2× SSC for 3 min. The colony blot filters were dried in a vacuum oven for 90 min at 80° C. and hybridized with radiolabeled pBluescript or the km-resistance gene, as described above. The colony blots were washed at 60° C. in 0.5× SSC and exposed to XAR-2 X-Ray film (Eastman Kodak, Rochester, N.Y.).

Gel electrophoresis and immunoblot analysis

Lysates of E. coli carrying pBluescript, pMC3 or pMC3:km or of H. pylori cells were prepared and analyzed by SDS-polyacrylamide gel electrophoresis (SDS-PAGE). Immunoblotting of whole cell extracts derived from wild-type and mutants 1, 21 and 22 was performed as detailed above using a 1:300 dilution of adsorbed human sera, and a 1:2000 dilution of goat anti-human immunoglobulin alkaline phosphatase conjugate as the secondary antibody, as described above. These studies showed that isogenic mutant strains 1, 21, and 22 have no antigenic tagA gene product.

Southern hybridizations

Southern hybridization of wild-type H. pylori strain 84–183 and kanamycin-resistant transformants M21 and M22 were performed. H. pylori chromosomal DNA was digested with HindIII or BamHI and SacI and the resulting fragments were electrophoresed on a 0.7% agarose gel and transferred to nylon membrane. Probes were gel-purified DNA fragments derived from pMC4 or pILL600 and were radiolabeled by primer extension using random hexameric oligonucleotides as described above. The DNA was then transferred to a nylon membrane and hybridized with $^{32}$p-labelled pMC4 or the 1.3 kb km cassette under conditions of high stringency. Hybridizations were performed in a solution of 6× SSC, 0.5% SDS, 5× Denhardt's solution and 100 μg/ml salmon sperm DNA and the blots were washed for 30 min. at 60° C. in 0.5× SSC/0.1% SDS.

Genotypic characterization of the transformants

To provide genetic evidence that the tagA gene is disrupted in the transformant strains, DNA isolated from wild-type strain 84–183 and *H. pylori* mutants 21 and 22 was digested with the restriction endonuclease HindIII or BamHI and SacI. After separation of the digested DNA on an agarose gel the DNA was transferred to a nylon membrane and hybridized to pMC4 which is a tagA probe. This probe hybridized to approximately 20 and 1.0 kb BamHI-SacI fragments in the wild-type strain, whereas the 1.0 kb BamHI-SacI fragment is lost and a new 2.3 kb hybridizing fragment was observed in both mutant strains without disruption of the other bands. Similarly, a 1.2 kb HindIII fragment was lost and a 2.2 kb fragment gained in both mutants because of the kanamycin resistance gene insertion. The kanamycin gene probe hybridized only with the 2.3 kb BamHI-SacI and 2.2 kb HindIII fragment in mutants 21 and 22 strains, which indicate that replacement had occurred in the tagA gene. Thus, the tagA gene in strain 84–183 had been mutagenized by insertion of the km gene.

Cytotoxin production

Cytotoxin production was assayed as described above and the results shown in Table 4. The results indicate that neither the intact TagA antigen nor the intact tagA gene is required for vacuolation.

TABLE 4

Cytotoxin production by wild-type *H. pylori* strains and tagA⁻ mutants

| Supernatant dilution | Optical density[a] | | | |
|---|---|---|---|---|
| | 84–183 | M1 | M22 | 87–203[b] |
| 1:5 | 0.21 ± 0.04 | 0.26 ± 0.04 | 0.23 ± 0.05 | 0 ± 0.02 |
| 1:10 | 0.16 ± 0.02 | 0.20 ± 0.03 | 0.13 ± 0.02 | 0.01 ± 0.01 |
| 1:20 | 0.13 ± 0.01 | 0.15 ± 0.02 | 0.10 ± 0.02 | 0.01 ± 0.01 |
| 1:40 | 0.09 ± 0.02 | 0.06 ± 0.01 | 0.06 ± 0.02 | 0.01 ± 0 |
| 1:80 | 0.03 ± 0.01 | 0.04 ± 0 | 0.02 ± 0.01 | 0.01 ± 0 |
| 1:160 | −0.01 ± 0.02 | −0.01 ± 0.01 | −0.01 ± 0.02 | −0.02 ± 0.02 |

[a]Net optical density as measured in neutral red assay of cytotoxin-induced vacuolation, as described above (59).
[b]Strain 87–203 is a strain known not to produce cytotoxin.

EXAMPLE 3

Full Length tagA Gene and Gene Product

Cloning and sequencing of the full length gene

Figure 3:
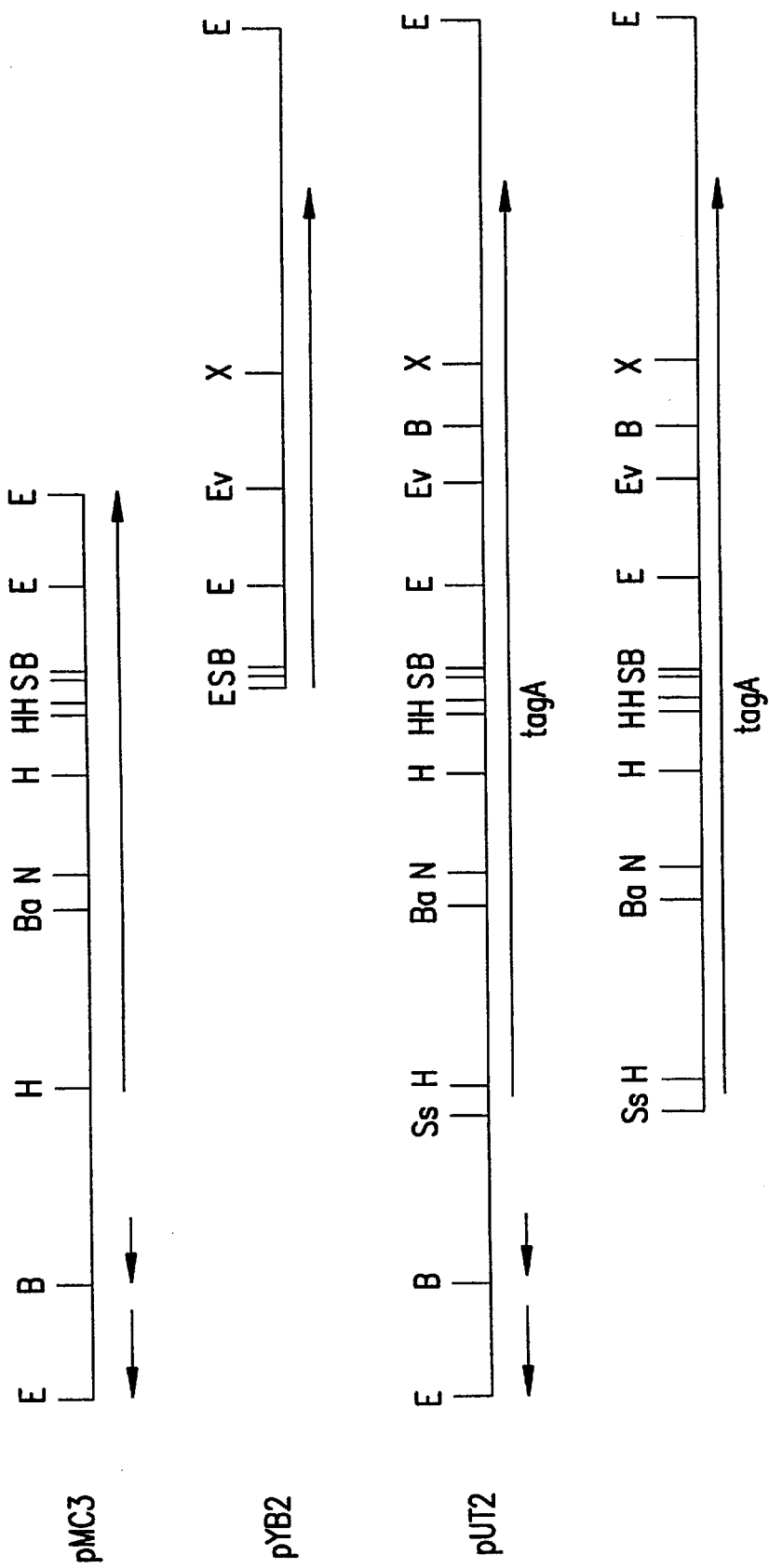
FIG. 3 shows physical maps of plasmids pMC3, pYB2 and pUT2. The large arrow beneath pUT2 represents the location of the tagA gene and the direction of transcription as determined by deletion mutations and immunoblotting. Restriction endonuclease cleavage sites: B, BglII; Ba, BamHI; E, EcoRI; EV, EcoRV; H, HindIII; N, NdeI; S, SacI, X; XbaI.
Figure 4:
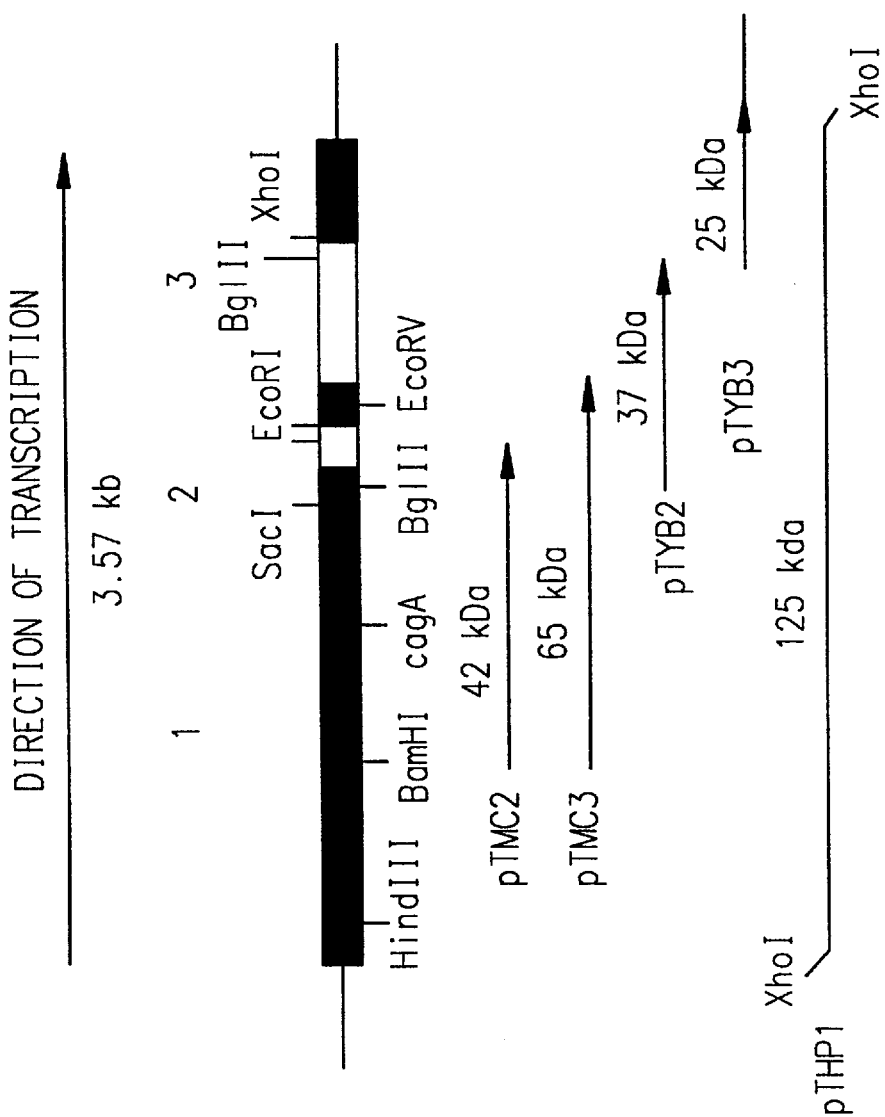
FIG. 4 shows physical mpas of the DNA fragments from tagA which were used to make overlapping gene fusions. The arrows represent the direction of transcription. The size of each product is indicated. The clear boxed areas represent those areas of the gene that possess repeated nucleotide regions and which have been determined to express immunogenic epitopes of this protein.

To isolate the full-length gene, we next used the 0.6 kb fragment of pYB1 as a probe to screen the λZapII library of *H. pylori* 84–183. Five positive plaques were purified and the pBluescript plasmids containing the cloned DNA inserts were excised by co-infection with the helper phage. Each of the five positive clones contained DNA inserts of 2 to 3 kb (data not shown). The clone designated pYB2, which contains a 2.7 kb insert, was chosen for further study and a restriction map generated (FIG. 3). A series of nested deletions starting at either end of the 2.7 kb insert of pYB2 was performed using exonuclease III. Using overlapping deletion clones of pYB2, we determined 1969 bp sequence in both strands. As expected, the first 785 bases of this sequence (SEQ ID NO:3, beginning with nucleotide 2864) overlapped with the end of pMC3. Translation of the complete nucleotide sequence generated from pMC3, pYB1 and pYB2 in all possible reading frames revealed a single open reading frame of 3,543 nucleotides initiated by an ATG codon at position 1072 and terminated by a TAA codon at position 4,615. The sequence encodes a protein of 1181 amino acid residues (SEQ ID NO:4) and the calculated molecular weight of the deduced polypeptide is 131,517 daltons. A sequence that could form a potential stem-loop structure in the mRNA and which could serve as a transcription termination site (ΔG=−14.4 Kcal) extends from nucleotides 4642 to 4674 (SEQ ID NO:3).

Homologies of the TagA polypeptide with other proteins

Search of Swiss.Prot version 21, and NBRF-PIR protein data banks showed no striking homologies with the full length TagA antigen (SEQ ID NO:4). However, among the homologies with the highest scores were chloroplast H⁺-transporting ATP synthases (62,63), and a sodium channel protein (74) with 16.8% and 17.3% identity, and 50% and 42.6% conserved amino acids in the region between residues 1–482 and 123–1182, respectively. No significant homologies were observed when the amino acid sequences of the other two ORFs contained in pMC3 were compared with the protein data bases.

The content of basic amino acids [141 lysines, (11.9%) and 117 asparagines (9.9%)] TagA was unusually high and was consistent with the predicted isoelectric point of the peptide (8.89). A hydropathicity plot indicated that the deduced protein is predominantly hydrophilic. An interesting feature of the primary structure of this protein is the presence of structures of homopolymeric amino acid sequence, most notably polyasparagine (SEQ ID NO:4, Position 3705). In searches comparing this asparagine-rich region with various protein sequence data bases, there was strong homology with sequences from yeast (64,65,66,67, 68,69,70) and Plasmodium (71) nucleotide-binding proteins. Polyasparagine is also found in the DNA-binding regulatory product of the lac9 gene of *Kluyveromyces var.lactis* (72) and potassium transport protein (TRK1) of *Saccharomyces cerevisiae* (73).

Construction of the full length tagA gene

To construct the full length tagA gene, we utilized the unique SacI restriction site located in both pMC3 and pYB2 (FIG. 3). First, the 3.6 kb tagA fragment of pMC3 was cloned into a pUC19 vector under the control of the lacZ prometer, to generate pUT1. Next, the 2.6 kb SacI fragment from pYB2 was cloned into sacI-digested pUT1. A clone with the correct orientation was selected, which was hamed pUT2. An identical clone (pEM3), but present in the pGEM3z vector, has been deposited with the ATCC in compliance with the requirements of the Budapest Treaty under Accession No. 69273. *E. coli* cells containing pUT2 or pEM3 expressed the immunoreactive *H. pylori* 128 kDa protein.

Detection of human serologic responses to the recombinant TagA protein by Western blotting To determine whether human sera reacted with the full-length recombinant TagA protein, lysate from pEM3-containing cells was electrophoresed on a 7% acrylamide gel, and electroblotted onto nitrocellulose paper. Sera from 10 *H. pylori* infected humans and 10 uninfected humans were diluted 1:100 and tested for reactivity with the recombinant protein. Sera from 7 *H. pylori* infected persons recognized the TagA protein, compared to sera from 1 of 10 uninfected persons (p=0.01, one-tailed Fisher's exact test). Thus, the recombinant full-length protein was a useful antigen for assessing human responses to *H. pylori*.

EXAMPLE 4

*H. pylori* strains possessing tagA associated with an increased risk of developing adenocarcinoma of the stomach This example describes a serologic assay to determine whether *Helicobacter pylori* infection is due to a tagA$^+$ strain. This serum IgG assay, utilizing orv220, a recombinant tagA fragment was found to have a sensitivity of 94.4% and specificity of 92.5% when used in a clinically-defined population.

The present example also shows that *H. pylori* infection is associated with gastric cancer risk. Serum specimens obtained from a cohort of Japanese-American men in Hawaii was used in a study of 103 *H. pylori*-infected men who eventually (13 years after the serum specimens were collected) developed gastric cancer, and 103 matched *H. pylori*-infected control specimens from the men who did not develop cancer within the same period of time. Serum antibodies to TagA were associated with a 1.9-fold (0.9–4.0, p=0.08) increased risk of developing gastric cancer during the observation period. Among the 75 men with intestinal type cancer of the distal stomach, the odds ratio (OR) was 2.3 (1.0–5.2, p=0.056). Young age (<72 years) and late stage at tumor diagnosis each were significantly associated with TagA-positivity.

The following results indicate that presence of serum antibodies to the product of a recombinant tagA accurately determines the tagA status of an infecting *H. pylori* strain, and indicates that infection with a tagA$^+$ strain is associated with an enhanced risk of development of gastric cancer, especially intestinal type affecting the distal stomach.

Selection of patients for validation study

To determine the utility of the TagA serologic assay, sera from 181 persons whose *H. pylori* status had been previously defined (9,22–24) were studied. Uninfected persons (n=115) were those who underwent endoscopy and had biopsies that did not reveal *H. pylori* infection by rapid urease test or by histologic examination; all patients also had negative serology in a standardized enzyme-linked immunosorbent assay (ELISA) for serum IgG directed to *H. pylori* (25). The 115 uninfected patients were arbitrarily divided into a reference group (n=35) and a test group (n=80). Infected persons were those from whom *H. pylori* was obtained in culture on biopsy; these 66 patients included those with duodenal ulceration (n=14), gastric ulceration (n=6), gastritis alone (n=36), or other diagnoses (n=10). For each patient, a single isolate was evaluated to determine tagA status by colony hybridization with a gene-specific probe, as previously described (6,24). On the basis of the hybridization assay, 36 patients were defined as being infected by a tagA$^+$ strain, and 30 patients by a tagA$^-$ strain. All sera had been stored at −20° C. until used.

Selection of patients for cancer study

All the patients in this study were part of the Japan-Hawaii Study cohort, as previously described. During the 21-year period from 1968–1989, 109 cases of pathologically-confirmed gastric carcinoma had been identified, and previous serologic testing indicated that 103 of these patients had been infected with *H. pylori* at the time of their original serum submission in the 1960's (5). Of the 103 matched controls for these cases, 83 had been *H. pylori*-infected. For each of the remaining 20 *H. pylori*-infected cases, 3 further controls were identified according to the previous criteria (5). Serology to determine whether *H. pylori* infection was present was done on coded samples, and from the positives, one *H. pylori*-infected control was randomly selected for each of the 20 unmatched cases. In total, the study consisted of 103 *H. pylori*-infected men who developed gastric cancer, and their 103 matched controls, who also were *H. pylori*-infected but did not develop gastric cancer during the study period.

Preparation of the recombinant TagA antigen

A 1.7kb BamHI fragment containing bp 1921–3648 of tagA cloned in pMC3 (16) was subcloned into the BamHI site of pET15b (Novagen, Madison Wis.), downstream of the T7 promoter. This plasmid (pORV220) was used to transform *E. coli* host strain BL21, a λDE3 lysogen containing the T7 RNA polymerase gene under control of the lacUV5 promoter (26). Addition of IPTG to a growing culture of the lysogen induces T7 polymerase to transcribe the target DNA on the recombinant plasmid. This vector allows transcriptionally-regulated expression of a fusion protein consisting of the TagA fragment with an N-terminal histidine-tag. The fusion protein consists of 600 residues (24 vector+576 insert), and has a predicted molecular mass of 66.4 kDa. The protein was purified from lysates of induced broth cultures using a nickel-chelating resin, and eluted with imidazole, as described (27).

Serologic methods

The presence of serum IgG antibodies to *H. pylori* was determined by ELISA with the Pyloristat kit (Biowhittaker, Walkersville, Md.) as previously described (5). For the TagA ELISAs, optimal concentrations of antigen, patient serum, and anti-human IgG conjugate were determined by checkerboard titrations. For orv220, the optimal antigen concentration was 5 μg/ml and 100 μl aliquots were loaded into wells in a 96-well microtiter plate. The optimal dilution of human serum was 1:100, and horseradish peroxidase-conjugated goat-anti-human IgG was used at a dilution of 1:4000. Other details of the serologic methods were exactly as described in similar assays (23,25).

Statistical analysis

The t-test for paired samples was used for the comparison of means, and McNemar's test was used for the comparison of the distribution of various characteristics between patients and control subjects. Odds ratios (OR) for stomach cancer, based on the results of the TagA assay, were derived from conditional logistic regression methods (29). Tests for linear trend in the logit of risk were derived from conditional logistic regression models through the use of grouped TagA test results (coded by quartile as 1, 2, 3, or 4). All models of conditional logistic regression were fitted by using iterative maximum likelihood methods and a special application of the proportional hazards regression model (30). The estimate of the attributable risk of gastric carcinoma related to a tagA$^+$ strain was based on the method of Walter (31). A receiver operator characteristic (ROC) curve was constructed to summarize the sensitivity and specificity estimates (32).

Diagnostic accuracy of TagA serology using orv220

Previous studies of TagA serology used a recombinant antigen that was purified from *E. coli* cell lysates (21). Because purification of this antigen was tedious and prolonged, overlapping tagA gene fragments were expressed as fusion proteins in an alternate prokaryotic expression system. Preliminary studies indicated that orv220 expressed the best of several of the candidate antigens based on the TagA fragments studied thus far. The truncated protein was compared with the antigen purified from *E. coli* strains transformed with pEM3, which encodes the entire tagA ORF. By linear regression analysis, serum IgG results for 41 persons (19 infected and 22 uninfected), correlated closely between assays using the 2 different antigens (r=0.96, p<0.001). Using the same threshold of the mean value for uninfected persons+2 SD, the orv220 antigen gave a negative result for 21 (95%) of the 22 uninfected persons; and the exception was weakly positive. For the 19 *H. pylori*-infected persons, the results with orv220 were exactly the same as for the pEM3 antigen (12 positive and 7 negative). Thus, serologic reactivity with the 66.4 kDa TagA fragment encoded by orv220 was nearly identical with that detected with a larger TagA fragment.

To establish the assay, sera from 36 persons known not to be infected with *H. pylori* were used for reference, and after multiple runs, thresholds based on mean values plus intervals of standard deviation were established. Concurrently, sera were tested from a second group of 80 uninfected persons, 36 persons known to be infected with a tagA$^+$ strain, and 30 persons from whom the only *H. pylori* isolate obtained was tagA$^-$. Not surprisingly, optical density ratios for the uninfected persons were nearly identical to those for the reference groups. In contrast, the values for the persons infected with tagA$^+$ strains were significantly higher (Students' T-test, p<0.001, one-tailed). Among the 30 sera obtained from persons from whom the only isolate was a tagA$^-$ strain, a bimodal distribution was observed. For 27 of the sera, the values were similar to those in the two groups of uninfected persons, but for three sera the values were much higher and similar to those for patients infected with tagA$^+$ strains.

To establish a threshold for use in diagnostic assays, the accuracy of several optical density ratio cut-offs were examined (Table 5). Overall, the highest accuracy was obtained when the mean value for the 35 uninfected (reference) patients+3 intervals of standard deviation was used, with sensitivity of 94.4% and specificity of 92.5%. This type of threshold was used in all future studies. On the basis of receiver operator characteristic (ROC) curves, there was high level discrimination of tagA status using orv220.

Assessment of stability of antibody levels

To determine whether serum antibodies to the TagA product persist over the course of chronic *H. pylori* infection, paired serum specimens from 36 epidemiologists who were part of a cohort previously studied for clinical and epidemiological features associated with *H. pylori* infection (28) were evaluated. On average, the specimens were obtained 7.59 years apart, and values in the standard *H. pylori* ELISA (28) were compared to values in the TagA ELISA.

Among 36 participants, none had seroconverted from positive to negative antibody status or vice versa. Mean optical density scores produced by the first and second sera were highly similar (0.217 vs 0.249; p=0.3, paired t-test; Table 6).

Association of tagA Positivity With Gastric Cancer

Having developed an assay to detect persons infected with *H. pylori* strains possessing TagA using TagA or antigenic fragments thereof, the invention shows that infection with a tagA$^+$ strain is associated with the risk of developing gastric cancer. From an earlier study of 109 Japanese-American patients, who developed gastric cancer over a 21-year observation period (5), 103 were found to be *H. pylori*-infected based on serum specimens obtained from them a mean of 13 years prior to cancer diagnosis. Each of these cases was matched to a control from the same cohort, of the same age, and who also was *H. pylori*-infected; the characteristics of the 103 *H. pylori* infected men who developed gastric cancer and their age-matched controls are shown in Table 7. The two groups of men were similar with respect to demographic characteristics and laboratory values.

For this population, presence of serum antibodies to TagA (i.e., infection with a tagA positive *H. pylori* strain) was associated with increased risk of cancer development (OR=1.9, p=0.08) (Table 8). An analysis confined to the 101 cases of cancer of the distal stomach and their controls showed highly similar values, as expected (OR=1.8, p=0.11). When the cases with distal cancers were stratified by the histologic type of tumor, the strongest association was with the intestinal type (OR=2.3, p=0.056) but not the diffuse type (OR=1.0, p=1.0); 3 men had an indeterminate histological pattern. Positivity in the TagA ELISA was not the result of seroconversion during the interval between when serum was obtained and diagnosis of cancer, nor was the magnitude of the TagA antibody response a factor in the risk developing cancer. In the population of *H. pylori*-infected persons, the presence of tagA was associated with an attributable risk of 28% (95% C.I.=0–57%) for gastric cancer. There was no association between levels of the IgG antibodies to TagA and levels of IgG to the conserved *H. pylori* antigens.

The TagA antibody analysis was stratified by the patients' age at which gastric cancer was diagnosed. TagA seropositivity was associated with a 3.0-fold (95% C.I.=1.0–9.3; p=0.057) increase in gastric cancer risk for 52 men diagnosed under the age of 72. In contrast, for 51 men who were ≧72 years at time of diagnosis, the association was not significant (OR=1.3, 95% C.I.=0.5–3.5). TagA seropositivity was associated with risk of developing an advanced stage tumor (3 or 4), OR=2.6, 95% C.I.=1.1–6.2; p=0.03, but not an earlier (1 or 2) stage tumor (OR=1.0). The risk of developing gastric cancer associated with TagA seropositivity was not increased when subjects were stratified according to birth order or sibship size.

Although some of the above OR values are not statistically significant using the conservative 2-tailed analysis of significance, use of 1-tailed analysis indicates that the associations with all cancers and intestinal type cancers reach statistical significance (p=0.04 and 0.028 respectively). Furthermore, undetected differences in risk between the two groups, lack of perfect accuracy of the assay, and variation in patient-to-patient response to this infection could help account for lack of significance.

Multiple infection

Simultaneous gastric infection with two *H. pylori* strains has been reported with frequencies of 10 to 13% (14,15), and simultaneous infection with three different strains also has been observed (33). In the initial validation study, only a single colony from each patient had been picked, so there was no opportunity to examine for multiple infection. However, that 3 of 30 (10%) persons from whom a tagA$^-$ strain was the only isolate had high-level serologic responses to TagA suggests that these persons were co-infected with a tagA$^+$ strain. Since only the conjunction of simultaneous infection with a tagA$^-$ index strain and a second tagA$^+$ strain and not vice versa, could show dichotomous results between colony testing and serologic assay, the data suggest that the frequency of multiple infection may be substantially higher than the previously reported frequency, which was based on a small number of biopsies (4,15).

The present Example further supports the utility of non-invasive serologic assays for *H. pylori* infections, because they are shown to be global assays that in essence sample the entire stomach. In contrast, biopsy-based techniques only sample a minuscule fraction (<<1%) of the gastric mucosa. Because TagA is an immunodominant antigen (17), serologic assays potentially have the power to detect infections with tagA$^+$ organisms even if numbers are low in relation to tagA$^-$ isolates.

The associations with the subset of more aggressive tumors (younger age, higher stage when diagnosed), and the consistency of the data with the underlying hypothesis, show that the effect is real as further supported by a number of realities of TagA biology. First, infection with tagA$^+$ strains is associated with enhanced epithelial cell injury (18,19), injury to surface gastric epithelial cells promoting or possibly initiating the oncogenesis. Second, infection with cagA$^+$ strains is associated with higher degrees of gastric inflammation (8,19), and with enhanced expression of pro-inflammatory cytokines such as IL-1 and IL-8 (19,35). These may contribute to epithelial injury. Third, most tagA$^+$ strains also express vacuolating cytotoxin activity (16,17). Expression of cytotoxin as assessed by serum neutralizing antibodies, may be associated with gastric cancer (36). Finally, intestinal type gastric cancer is more highly associated with increased inflammation and atrophic gastritis than is the diffuse type (37,38).

It has been shown that high titered antibody responses to conserved H. pylori antigens were associated with gastric cancer risk (5,8). One interpretation of this phenomenon is that high antibody levels are markers for the degree of inflammation, active inflammation being considered a precursor of oncogenic events (1). The lack of strict correlation of gastric cancer and anti-TagA antibody levels may reflect overmatching, since only persons infected with H. pylori were selected, all of whom have some degree of inflammation. In any event, the significance of these findings must be tempered by the observation that TagA-positivity was present in 78% of the H. pylori-infected controls who did not develop cancer. Thus, infection with a tagA$^+$ strain is neither necessary nor sufficient for oncogenesis but is shown to be a factor involved in this process.

The presence of tagA in a strain may be a marker for adjacent genes or for a particular phenotype that itself is relevant to inflammation or to the oncogenic process. Nevertheless, this Example shows that particular H. pylori strains are associated with differential risk of gastric cancer.

Summary

Among persons known to be infected with tagA$^+$ strains, there was a broad range in serologic reactivity, but without substantial overlap with the reactivity of uninfected persons. The stability of the results over years in the absence of antimicrobial therapy further indicates the utility of the present TagA assay.

Having provided an accurate assay for detecting infection with a tagA$^+$ strain of H. pylori, the invention also permitted the determination that infection with a tagA$^+$ strain is a risk factor for the development of gastric cancer. Infection with a tagA$^+$ strain nearly doubled the risk of developing gastric cancer over the ensuing 21 years, compared with infection with tagA$^-$ strain, and the effect was more marked for persons who developed intestinal type neoplasms.

Having provided a purified TagA and antigenic fragments of TagA, and shown that infection with a TagA expressing strain indicates predisposition to gastric carcinoma, further uses of the present discoveries are enabled.

TABLE 5

Diagnostic value of TagA ELISA using orv220

| Group | Number of subjects | Number (%) exceeding threshold* | | | |
|---|---|---|---|---|---|
| | | 1SD | 2SD | 3SD | 4SD |
| Uninfected | 80 | 12(15%) | 9(11.3%) | 6(7.5%) | 3(3.8%) |
| Infected, tagA$^-$ strain | 30 | 9(30%) | 6(20%) | 5(16.7%) | 4(13.3.%) |
| Infected, tagA$^+$ strain | 36 | 36(100%) | 3597.2%) | 3494.4%) | 31(86.1%) |

*Threshold defined as mean plus stated intervals of standard deviation (SD) of optical density ratio (ODR) values for reference group of 35 persons known not to be infected by H. pylori.

TABLE 6

Stability of serum antibodies to H. pylori antigens in 36 subjects

| | Serum IgG response to indicated antigen | |
|---|---|---|
| Serum specimen | Conserved H. pylori antigens** | TagA† |
| Initial | 3260 | 0.217 ± 0.30 |
| Follow-up* | 2913 | 0.249 ± 0.35 |

*Follow-up specimen obtained an average of 7.59 ± 1.0 years after initial specimen.
**Antibody level indicated by reciprocal geometric mean titer to pool of sonicates of 5 H. pylori strains.
†Antibody level indicated by Mean ± SD optical density ratio.

TABLE 7

Characteristics of H. pylori-infected patients with gastric cancer and control subjects at the time the serum specimen was obtained

| Characteristic | Patients (n = 103) | Controls (n = 103) | P-value |
|---|---|---|---|
| Mean age at examination (year) | 58.8 | 58.7 | 0.18 |
| Born in United States (%) | 83 | 83 | 0.83 |
| Married (%) | 93 | 95 | 0.72 |
| Alcohol use (%) | 65 | 73 | 0.27 |
| Mean body-mass index | 23.5 | 24.0 | 0.33 |
| Mean diastolic blood pressure (mm Hg) | 81.6 | 82.1 | 0.74 |
| Mean serum cholesterol (mmol/liter) | 5.7 | 5.6 | 0.74 |
| Mean serum glucose (mmol/liter) | 9.3 | 9.2 | 0.92 |

TABLE 8

Odds Ratios for the Association between Infection with a tagA$^+$ H. pylori Strain and Gastric Cancer

| Gastric Cancer Type | Matched-pair Status[a] (Patients/Controls) | | | | Total | Odds Ratio | 95% Confidence Interval[b] |
|---|---|---|---|---|---|---|---|
| | +/+ | +/− | −/+ | −/− | | | |
| All | 69 | 21 | 11 | 2 | 103 | 1.9 | (0.9–4.0) |
| Distal | 68 | 20 | 11 | 2 | 101 | 1.8 | (0.9–3.8) |

TABLE 8-continued

Odds Ratios for the Association between Infection with a tagA⁺ *H. pylori* Strain and Gastric Cancer

| Gastric Cancer Type | Matched-pair Status[a] (Patients/Controls) | | | | Total | Odds Ratio | 95% Confidence Interval[b] |
|---|---|---|---|---|---|---|---|
| | +/+ | +/− | −/+ | −/− | | | |
| Intestinal | 48 | 18 | 8 | 1 | 75 | 2.3 | (1.0–5.2) |
| Diffuse | 18 | 2 | 2 | 1 | 23 | 1.0 | (0.1–7.1) |

[a]+/+, both patient and matched control show serologic response to TagA.
+/−, patient but not matched control show serologic response to TagA.
−/+, control but not patient show serologic response to TagA.
−/−, neither patient nor control show serologic response to TagA.
[b]two-tailed analysis Throughout this application various publications are referenced. The disclosures of these publications in their entireties are hereby incorporated by reference into this application in order to more fully describe the state of the art to which this invention pertains.

REFERENCES

1. Blaser M. J., Parsonnet J. *J Clin Invest* 94:4–8, 1994.
2. Correa P. *N Engl J Med* 325:1170–1171, 1991.
3. Talley et al. J Nat Cancer Instit 83:1734–1739, 1991.
4. Parsonnet et al. *N Engl J Med* 325:1127–1131, 1991.
5. Nomura et al. *N Engl J Med* 325:1132–1136, 1991.
6. Forman et al. *Int J Cancer* 46:608–611, 1990.
7. EUROGAST Study *Group Lancet* 341:1359–1362, 1993.
8. Asaka et al. Cancer 73:2691–2694, 1994.
9. Sipponen et al. *Scand J Gastroenterol Suppl* 196:S3–S6, 1993.
10. Forman et al. *BMJ* 302:1302–1305, 1991.
11. Correa P. *Cancer Res* 52:6735–6740, 1992.
12. Taylor D. N., Blaser M. J. *Epidemiologic Rev* 13:42–59, 1991.
13. Akopyanz et al. *Nucleic Acids Res* 20:5137–5142, 1992.
14. Fujimoto et al. *J Clin Microbiol* 32:331–334, 1994.
15. Prewett et al. *Gastroenterol* 102:829–833, 1992.
16. Tummuru et al. *Infect Immun* 61:1799–1809, 1993.
17. Covacci et al. *Proc Natl Acad Sci USA* 90:5791–5795, 1993.
18. Crabtree et al. *Lancet* 338:332–335, 1991.
19. Peek et al. *Gastroenterol* 1994; (In Press)
20. Cover et al. *Infect Immun* 58:603–610, 1990.
21. Cover et al. "The 120–128 kDa cytotoxin-associated protein (CagA) as a marker for ulcerogenic *Helicobacter pylori* strains" Abstract presented at the Annual Meeting of the American Gastroenterological Association, New Orleans, La., May 1994.
22. Dooley et al. N Engl J Med 321:1562–1566, 1989.
23. Cover et al. *J Clin Invest* 90:913–918, 1992.
24. Peek R. M., Jr. *J Clin Microbiol* 1994;
25. Pérez-Pérez et al. *Ann Intern Med* 109:11–17, 1988.
26. Studier et al. *J Mol Biol* 189:113–130, 1986.
27. Baier et al. *Biotechniques* 17:94–99, 1994.
28. Parsonnet et al. *Gastroenterol* 102:41–46, 1992.
29. Breslow et al. *International Agency for Research on Cancer* 247–276, 1980.
30. Harrell F. E., Jr. The PHGLM procedure, in Joyner S. P. (ed): *SUGI supplemental library user's guide.* Cary, N. C., SAS Institute; 1983:267–294.
31. Walter S. *Int J Epidemiol* 7:175–182, 1978.
32. ROC
33.. Fox et al. *American Society for Microbiology*, Washington, D.C.
34. Worth et al. *J Chronic Dis* 23:389–397, 1970.
35. Crabtree et al. *Journal of Clinical Pathology* 47:61–66, 1994.
36. Hirai et al. *Int J Cancer* 56:56–60, 1994.
37. Sipponen P, Lauren: *Scand J Gastroenterol* 29:336–340, 1994.
38. Sipponen et al. *J Gastroenterol Hepatol* 6:244–248, 1991.
39. Leunk et al. *J. Med. Microbial.* 26:93–99,1988
40. Figura et al. *J. Clin. Microbiol.* 27:225–226, 1988
41. Cover and Blaser *J. Biol. Chem.* 267:10570–10575, 1992
42. Apel et al. *Zbl. Bakt. Hyg.* A. 268:217–276, 1988
43. Gerstenecker et al. *Eur. J. Clin. Microbiol. Infect. Dis.* 11(7):595–601, 1992
44. Kunkel et al. *Methods Enzymol.* 1987:154:367, 1987
45. Brake et al., 1984
46. Harlow and Lane, *Antibodies; A Laboratory Manual,* Cold Spring Harbor Laboratory, Cold Spring Harbor, N.Y., 1988
47. Donnenberg and Kaper *Infect. Immun.* 4310–4317, 1991
48. Arnon, R. (Ed.) *Synthetic Vaccines* I:83–92, CRC Press, Inc., Boca Raton, Fla., 1987
49. Birnboim and Doly (*Nucleic Acids. Res.,* 7:1513–1523, 1999
50. Sambrdok et al. *Molecular cloning: A Laboratory Manual,* 1989
51. Sanger et al. *Proc. Natl. Acad. Sci. U.S.A.,* 71:1342–1346.32, 1977
52. Hawley and McClure *Nucleic Acids Res.* 11:2237–2255, 1983
53. Blaser and Gotschlich *J. Biol. Chem.* 265:14529–14535, 1990
54. Short et al. *Nucleic Acids Res.,* 16:7583–7600, 1988
55. Blaser et al. *Infect. Immun.,* 42:276–284, 1983
56. Oakley et al. (*Anal. Biochem.* 105:361–363, 1980
57. Feinberg and Bogelstein *Anal. Biochem,* 132:6–13, 1983
58. Montefiori et al. *J. Clin. Microbiol.* 26:231–235, 1988
59. Cover et al. *Infect. Immun.* 59:1264–1270, 1991
60. Labigne-Roussel et al. *J. Bacteriol.,* 170:1704, 1988
61. Ferrero et al. *J. Bacteriol.,* 174:4212, 1992
62. Hiratsuka et al. *Mol. Gen. Genet.* 217:185–194, 1989
63. Rodermel and Bogorad *Genetics,* 116:127–139, 1987
64. Forsburg and Guarente *Genes Dev.* 3:1166–1178, 1989
65. Hudspeth et al. *Cell* 30:617–626, 1982
66. Ju et al. *Mol. Cell. Biol.* 10:5226–5234, 1990
67. O'Hara et al. *Nucleic Acids Res.* 16:10133–10170, 1988
68. Rhode et al. *Genes Dev.* 3:1926–1939, 1989
69. Tanaka et al. *Mol. Cell. Biol.* 9:757–768, 1989
70. Toda et al. *Genes Dev.* 2:517–527, 1988
71. Stahl et al. *Nucleic Acids Res.* 14:3089–3102, 1986
72. Salmeron and Johnston *Nucleic Acids Res.* 14:7767–7781, 1986
73. Gaber et al. *Mol. Cell. Biol.* 8:2848–2859, 1989
74. Trimmer et a. *Neutrol* 3:33–49, 1989
75. Ferretti et al. *Proc. Natl. Acad. Sci.* 82:599–603, 1986
76. Wosnick et al. *Gene* 76:153–160, 1989

What is claimed is:

1. An antigenic polypeptide comprising the amino acids encoded by nucleotides 1921–3648 as shown in SEQ ID NO:1.

2. The polypeptide of claim 1, wherein the polypeptide is a fusion protein.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 3648 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Helicobacter pylori ( i x ) FEATURE:
        ( A ) NAME/KEY: CDS
        ( B ) LOCATION: 1072..3648

( x i ) SEQUENCE DESCRIPTION: SEQ ID NO:1:

```
ATGGGCTGCG  CGTAACGAAA  AACAGTCGCT  TGACCTCTTT  TGATGTCATC  AGAGATTTTC    60

CAAATATCCG  CTATACCTTT  GACTCCTAGA  GCGCAACCAC  CTACGATCGC  TAGAACAGAA   120

ATGATCTGAA  CCACCAAAGT  TTTAGTCTCA  GTAATGCCTG  ATGCAGGACT  GTCGAAAGCC   180

ATTAAAGGAT  TGGCTGCTAT  CGCTAGCCCT  AAAGTTACTA  CAACTTTCTT  GTAGCTGTCA   240

GTGATTCTTG  TAAAAAATTT  CATGCGTTTC  CTTTCAAATT  GAAATCAATC  GTTTGAGTAT   300

ATCAAAAAAA  AGTATTTTTA  TACTATTCAT  ACAAGCGCTA  CTTTATAATT  TAAATCAAAA   360

CCGACGCTTT  TGTTTGACAA  CTGATATAAT  TTAGGAACAA  TAAACCTACT  TGTCCCAACC   420

ATTTTTCTTT  CTCAAGTCAT  CGTAGAATTG  TAGATCTTTA  GGATCTTTGA  TGTATTTTTT   480

AATCGTCTCA  GGTTGAAACC  TAAAAACAAG  CAGAAACAAA  CCCAAGCTGA  TCAGAGTGAG   540

AATAAAGCTC  CATTTTAAGC  AACTCCATAA  ACCACTAAAG  AAACTTTTTT  TGAGACTCTC   600

TTTGAAAATC  TGTCCTATTG  ATTTGTTTTC  CATTTTGTTT  CCCATGCGGA  TCACAAACGC   660

TTAATTACAA  ATACATACTA  TAATAAGTAT  GGCACACACA  AACCAAACCA  TTTTTAGAAC   720

GCTTCATGCA  CTCACCTTGC  TCCTAACCAT  TTCTCCAACC  ATCTTTAGCG  TTGCATTTGA   780

TTTCTTCAAA  AAGGCTCATT  TCTTAGTTTC  TTTTATTCTT  AAAATTTTTC  CATTCTAGCA   840

AATTTTTGTT  AATTGTGGGT  AAAAATGTGA  ATCGTTCCTA  GCTTTTAGAC  GCTTGCAACG   900

ATCGGACTTT  TTTCAATATT  AATGAAAAAA  TGCCAAATAT  TCTAAATATT  GTGGTATAGT   960

GATAACGTTC  AAAGACACGA  ATTGCATACT  CAAAGTGTGT  AGTAGTTTTT  AGCGGTCTTT  1020

GATACCAATA  AGATACCGAT  AGGTATGAAA  CTAGGTATAG  AAGGAGAAAC  A ATG ACT  1077
                                                            Met Thr
                                                              1
```

| | | | | | | | | | | | | | | | | |
|---|---|---|---|---|---|---|---|---|---|---|---|---|---|---|---|---|
| AAC | GAA | ACT | ATT | GAC | CAA | CAA | CCA | CAA | ACC | GAA | GCG | GCT | TTT | AAC | CCG | 1125 |
| Asn | Glu | Thr | Ile | Asp | Gln | Gln | Pro | Gln | Thr | Glu | Ala | Ala | Phe | Asn | Pro | |
| | | 5 | | | | | 10 | | | | | 15 | | | | |
| CAG | CAA | TTT | ATC | AAT | AAT | CTT | CAA | GTA | GCT | TTT | CTT | AAA | GTT | GAT | AAC | 1173 |
| Gln | Gln | Phe | Ile | Asn | Asn | Leu | Gln | Val | Ala | Phe | Leu | Lys | Val | Asp | Asn | |
| | 20 | | | | | 25 | | | | | 30 | | | | | |
| GCT | GTC | GCT | TCA | TAC | GAT | CCT | GAT | CAA | AAA | CCA | ATC | GTT | GAT | AAG | AAC | 1221 |
| Ala | Val | Ala | Ser | Tyr | Asp | Pro | Asp | Gln | Lys | Pro | Ile | Val | Asp | Lys | Asn | |
| 35 | | | | | 40 | | | | 45 | | | | | | 50 | |
| GAT | AGG | GAT | AAC | AGG | CAA | GCT | TTT | GAG | GGA | ATC | TCG | CAA | TTA | AGG | GAA | 1269 |
| Asp | Arg | Asp | Asn | Arg | Gln | Ala | Phe | Glu | Gly | Ile | Ser | Gln | Leu | Arg | Glu | |
| | | | | 55 | | | | | 60 | | | | | 65 | | |

| | | | | | | | | | | | | | | | | |
|---|---|---|---|---|---|---|---|---|---|---|---|---|---|---|---|---|
|GAA|TAC|TCC|AAT|AAA|GCG|ATC|AAA|AAT|CCT|ACC|AAA|AAG|AAT|CAG|TAT|1317|
|Glu|Tyr|Ser|Asn|Lys|Ala|Ile|Lys|Asn|Pro|Thr|Lys|Lys|Asn|Gln|Tyr| |
| | | |70| | | |75| | | | |80| | | | |
|TTT|TCA|GAC|TTT|ATC|AAT|AAG|AGC|AAT|GAT|TTA|ATC|AAC|AAA|GAC|AAT|1365|
|Phe|Ser|Asp|Phe|Ile|Asn|Lys|Ser|Asn|Asp|Leu|Ile|Asn|Lys|Asp|Asn| |
| | | |85| | | |90| | | | |95| | | | |
|CTC|ATT|GTC|GTG|GAA|TCT|TCC|ACA|AAG|AGC|TTT|CAG|AAA|TTT|GGG|GAT|1413|
|Leu|Ile|Val|Val|Glu|Ser|Ser|Thr|Lys|Ser|Phe|Gln|Lys|Phe|Gly|Asp| |
|100| | | | |105| | | | |110| | | | | | |
|CAG|CGT|TAC|CGA|ATT|TTC|ACA|AGT|TGG|GTG|TCC|CAT|CAA|AAC|GAT|CCG|1461|
|Gln|Arg|Tyr|Arg|Ile|Phe|Thr|Ser|Trp|Val|Ser|His|Gln|Asn|Asp|Pro| |
|115| | | | |120| | | | |125| | | | |130| |
|TCT|AAA|ATC|AAC|ACC|CGA|TGC|ATC|CGA|AAT|TTT|ATG|GAA|CAT|ACC|ATA|1509|
|Ser|Lys|Ile|Asn|Thr|Arg|Cys|Ile|Arg|Asn|Phe|Met|Glu|His|Thr|Ile| |
| | | | |135| | | | |140| | | | |145| | |
|CAA|CCC|CCT|ATC|CCT|GAT|GAC|AAA|GAA|AAA|GCA|GAG|TTT|TTG|AAA|TCT|1557|
|Gln|Pro|Pro|Ile|Pro|Asp|Asp|Lys|Glu|Lys|Ala|Glu|Phe|Leu|Lys|Ser| |
| | | |150| | | |155| | | | |160| | | | |
|GCC|AAA|CAA|TCT|TTT|GCA|GGA|ATC|ATC|ATA|GGG|AAT|CAA|ATC|CGA|ACG|1605|
|Ala|Lys|Gln|Ser|Phe|Ala|Gly|Ile|Ile|Ile|Gly|Asn|Gln|Ile|Arg|Thr| |
| | |165| | | | |170| | | | |175| | | | |
|GAT|CAA|AAA|TTC|ATG|GGC|GTG|TTT|GAT|GAA|TCC|TTG|AAA|GAA|AGG|CAA|1653|
|Asp|Gln|Lys|Phe|Met|Gly|Val|Phe|Asp|Glu|Ser|Leu|Lys|Glu|Arg|Gln| |
|180| | | | |185| | | | |190| | | | | | |
|GAA|GCA|GAA|AAA|AAT|GGA|GGG|CCT|ACT|GGT|GGG|GAT|TGG|TTG|GAT|ATT|1701|
|Glu|Ala|Glu|Lys|Asn|Gly|Gly|Pro|Thr|Gly|Gly|Asp|Trp|Leu|Asp|Ile| |
|195| | | | |200| | | | |205| | | | |210| |
|TTT|TTA|TCA|TTT|ATA|TTT|GAC|AAA|AAA|CAA|TCT|TCT|GAT|GTC|AAA|GAA|1749|
|Phe|Leu|Ser|Phe|Ile|Phe|Asp|Lys|Lys|Gln|Ser|Ser|Asp|Val|Lys|Glu| |
| | | | |215| | | | |220| | | | |225| | |
|GCA|ATC|AAT|CAA|GAA|CCA|CTT|CCT|CAT|GTC|CAA|CCA|GAT|ATA|GCC|ACT|1797|
|Ala|Ile|Asn|Gln|Glu|Pro|Leu|Pro|His|Val|Gln|Pro|Asp|Ile|Ala|Thr| |
| | | |230| | | |235| | | | |240| | | | |
|AGC|ACC|ACT|CAC|ATA|CAA|GGC|TTA|CCG|CCT|GAA|TCT|AGG|GAT|TTG|CTT|1845|
|Ser|Thr|Thr|His|Ile|Gln|Gly|Leu|Pro|Pro|Glu|Ser|Arg|Asp|Leu|Leu| |
| | |245| | | | |250| | | | |255| | | | |
|GAT|GAA|AGG|GGT|AAT|TTT|TCT|AAA|TTC|ACT|CTT|GGC|GAT|ATG|GAA|ATG|1893|
|Asp|Glu|Arg|Gly|Asn|Phe|Ser|Lys|Phe|Thr|Leu|Gly|Asp|Met|Glu|Met| |
|260| | | | |265| | | | |270| | | | | | |
|TTA|GAT|GTT|GAG|GGC|GTC|GCC|GAC|ATG|GAT|CCC|AAT|TAC|AAG|TTC|AAT|1941|
|Leu|Asp|Val|Glu|Gly|Val|Ala|Asp|Met|Asp|Pro|Asn|Tyr|Lys|Phe|Asn| |
|275| | | | |280| | | | |285| | | | |290| |
|CAA|TTA|TTG|ATT|CAC|AAT|AAC|ACT|CTG|TCT|TCT|GTG|TTA|ATG|GGG|AGT|1989|
|Gln|Leu|Leu|Ile|His|Asn|Asn|Thr|Leu|Ser|Ser|Val|Leu|Met|Gly|Ser| |
| | | | |295| | | | |300| | | | |305| | |
|CAT|GAT|GGC|ATA|GAA|CCT|GAA|AAA|GTT|TCA|TTA|TTG|TAT|GCG|GGC|AAT|2037|
|His|Asp|Gly|Ile|Glu|Pro|Glu|Lys|Val|Ser|Leu|Leu|Tyr|Ala|Gly|Asn| |
| | | |310| | | |315| | | | |320| | | | |
|GGT|GGT|TTT|GGA|GCC|AAG|CAC|GAT|TGG|AAC|GCC|ACC|GTT|GGT|TAT|AAA|2085|
|Gly|Gly|Phe|Gly|Ala|Lys|His|Asp|Trp|Asn|Ala|Thr|Val|Gly|Tyr|Lys| |
| | |325| | | | |330| | | | |335| | | | |
|GAC|CAA|CAA|GGT|AAC|AAT|GTG|GCT|ACA|ATA|ATT|AAT|GTG|CAT|ATG|AAA|2133|
|Asp|Gln|Gln|Gly|Asn|Asn|Val|Ala|Thr|Ile|Ile|Asn|Val|His|Met|Lys| |
|340| | | | |345| | | | |350| | | | | | |
|AAC|GGC|AGT|GGC|TTA|GTC|ATA|GCA|GGT|GGT|GAG|AAA|GGG|ATT|AAC|AAC|2181|
|Asn|Gly|Ser|Gly|Leu|Val|Ile|Ala|Gly|Gly|Glu|Lys|Gly|Ile|Asn|Asn| |
|355| | | | |360| | | | |365| | | | |370| |
|CCT|AGT|TTT|TAT|CTC|TAC|AAA|GAA|GAC|CAA|CTC|ACA|GGC|TCA|CAA|CGA|2229|
|Pro|Ser|Phe|Tyr|Leu|Tyr|Lys|Glu|Asp|Gln|Leu|Thr|Gly|Ser|Gln|Arg| |
| | | |375| | | | |380| | | | |385| | | |

| | | | | | | | | | | | | | | | | |
|---|---|---|---|---|---|---|---|---|---|---|---|---|---|---|---|---|
|GCA|TTG|AGT|CAA|GAA|GAG|ATC|CAA|AAC|AAA|ATA|GAT|TTC|ATG|GAA|TTT|2277|
|Ala|Leu|Ser|Gln|Glu|Glu|Ile|Gln|Asn|Lys|Ile|Asp|Phe|Met|Glu|Phe| |
| | |390| | | | |395| | | |  | |400| | | |
|CTT|GCA|CAA|AAC|AAT|GCT|AAA|TTA|GAC|AGC|TTG|AGC|GAG|AAA|GAG|AAA|2325|
|Leu|Ala|Gln|Asn|Asn|Ala|Lys|Leu|Asp|Ser|Leu|Ser|Glu|Lys|Glu|Lys| |
| | |405| | | | |410| | | | |415| | | | |
|GAA|AAA|TTC|CGA|AAT|GAG|ATT|AAG|GAT|TTC|CAA|AAA|GAC|TCT|AAG|CCT|2373|
|Glu|Lys|Phe|Arg|Asn|Glu|Ile|Lys|Asp|Phe|Gln|Lys|Asp|Ser|Lys|Pro| |
|  |420| | | | |425| | | | |430| | | | | |
|TAT|TTA|GAC|GCC|CTA|GGG|AAT|GAT|CGT|ATT|GCT|TTT|GTT|TCT|AAA|AAA|2421|
|Tyr|Leu|Asp|Ala|Leu|Gly|Asn|Asp|Arg|Ile|Ala|Phe|Val|Ser|Lys|Lys| |
|435| | | | |440| | | | |445| | | | |450| |
|GAC|CCA|AAA|CAT|TCA|GCT|TTA|ATT|ACT|GAG|TTT|AAT|AAG|GGG|GAT|TTG|2469|
|Asp|Pro|Lys|His|Ser|Ala|Leu|Ile|Thr|Glu|Phe|Asn|Lys|Gly|Asp|Leu| |
| | | | |455| | | | |460| | | | |465| | |
|AGC|TAC|ACT|CTC|AAA|GTT|ATG|GGA|AAA|AAG|CAG|ATA|AAG|GCT|TTA|GAT|2517|
|Ser|Tyr|Thr|Leu|Lys|Val|Met|Gly|Lys|Lys|Gln|Ile|Lys|Ala|Leu|Asp| |
| | | |470| | | | |475| | | | |480| | | |
|AGG|GAG|AAA|AAT|GTC|ACT|CTT|CAA|GGT|AAC|CTA|AAA|CAT|GAT|GGC|GTG|2565|
|Arg|Glu|Lys|Asn|Val|Thr|Leu|Gln|Gly|Asn|Leu|Lys|His|Asp|Gly|Val| |
| | |485| | | | |490| | | | |495| | | | |
|ATG|TTT|GTT|AAT|TAT|TCT|AAT|TTC|AAA|TAC|ACC|AAC|GCC|TCC|AAG|AGT|2613|
|Met|Phe|Val|Asn|Tyr|Ser|Asn|Phe|Lys|Tyr|Thr|Asn|Ala|Ser|Lys|Ser| |
|  |500| | | | |505| | | | |510| | | | | |
|CCC|AAT|AAG|GGT|GTA|GGC|GTT|ACG|AAT|GGC|GTT|TCC|CAT|TTA|GAA|GCA|2661|
|Pro|Asn|Lys|Gly|Val|Gly|Val|Thr|Asn|Gly|Val|Ser|His|Leu|Glu|Ala| |
|515| | | | |520| | | | |525| | | | |530| |
|GGC|TTT|AGC|AAG|GTG|GCT|GTC|TTT|AAT|TTG|CCT|AAT|TTA|AAT|AAT|CTC|2709|
|Gly|Phe|Ser|Lys|Val|Ala|Val|Phe|Asn|Leu|Pro|Asn|Leu|Asn|Asn|Leu| |
| | | | |535| | | | |540| | | | |545| | |
|GCT|ATC|ACT|AGT|GTC|GTA|AGG|CGG|GAT|TTA|GAG|GAT|AAA|CTA|ATC|GCT|2757|
|Ala|Ile|Thr|Ser|Val|Val|Arg|Arg|Asp|Leu|Glu|Asp|Lys|Leu|Ile|Ala| |
| | | |550| | | | |555| | | | |560| | | |
|AAA|GGA|TTG|TCC|CCA|CAA|GAA|GCT|AAT|AAG|CTT|GTC|AAA|GAT|TTT|TTG|2805|
|Lys|Gly|Leu|Ser|Pro|Gln|Glu|Ala|Asn|Lys|Leu|Val|Lys|Asp|Phe|Leu| |
| | |565| | | | |570| | | | |575| | | | |
|AGT|AGC|AAC|AAA|GAA|TTG|GTT|GGA|AAA|GCT|TTA|AAC|TTC|AAT|AAA|GCT|2853|
|Ser|Ser|Asn|Lys|Glu|Leu|Val|Gly|Lys|Ala|Leu|Asn|Phe|Asn|Lys|Ala| |
|  |580| | | | |585| | | | |590| | | | | |
|GTA|GCT|GAA|GCT|AAA|AAC|ACA|GGC|AAC|TAT|GAC|GAG|GTG|AAA|CGA|GCT|2901|
|Val|Ala|Glu|Ala|Lys|Asn|Thr|Gly|Asn|Tyr|Asp|Glu|Val|Lys|Arg|Ala| |
|595| | | | |600| | | | |605| | | | |610| |
|CAG|AAA|GAT|CTT|GAA|AAA|TCT|CTA|AAG|AAA|CGA|GAG|CAT|TTG|GAG|AAA|2949|
|Gln|Lys|Asp|Leu|Glu|Lys|Ser|Leu|Lys|Lys|Arg|Glu|His|Leu|Glu|Lys| |
| | | | |615| | | | |620| | | | |625| | |
|GAT|GTA|GCG|AAA|AAT|TTG|GAG|AGC|AAA|AGC|GGC|AAC|AAA|AAT|AAA|ATG|2997|
|Asp|Val|Ala|Lys|Asn|Leu|Glu|Ser|Lys|Ser|Gly|Asn|Lys|Asn|Lys|Met| |
| | | |630| | | | |635| | | | |640| | | |
|GAA|GCA|AAA|GCT|CAA|GCT|AAC|AGC|CAA|AAA|GAT|GAG|ATT|TTT|GCG|TTG|3045|
|Glu|Ala|Lys|Ala|Gln|Ala|Asn|Ser|Gln|Lys|Asp|Glu|Ile|Phe|Ala|Leu| |
| | |645| | | | |650| | | | |655| | | | |
|ATC|AAT|AAA|GAG|GCT|AAT|AGA|GAC|GCA|AGA|GCA|ATC|GCT|TAC|GCT|CAA|3093|
|Ile|Asn|Lys|Glu|Ala|Asn|Arg|Asp|Ala|Arg|Ala|Ile|Ala|Tyr|Ala|Gln| |
|  |660| | | | |665| | | | |670| | | | | |
|AAT|CTT|AAA|GGC|ATC|AAA|AGG|GAA|TTG|TCT|GAT|AAA|CTT|GAA|AAT|ATC|3141|
|Asn|Leu|Lys|Gly|Ile|Lys|Arg|Glu|Leu|Ser|Asp|Lys|Leu|Glu|Asn|Ile| |
|675| | | | |680| | | | |685| | | | |690| |
|AAC|AAG|GAT|TTG|AAA|GAC|TTT|AGT|AAA|TCT|TTT|GAT|GGA|TTC|AAA|AAT|3189|
|Asn|Lys|Asp|Leu|Lys|Asp|Phe|Ser|Lys|Ser|Phe|Asp|Gly|Phe|Lys|Asn| |
| | | | |695| | | | |700| | | | |705| | |

```
GGC  AAA  AAT  AAG  GAT  TTC  AGC  AAG  GCA  GAA  GAA  ACG  CTA  AAA  GCC  CTT     3237
Gly  Lys  Asn  Lys  Asp  Phe  Ser  Lys  Ala  Glu  Glu  Thr  Leu  Lys  Ala  Leu
               710                      715                     720

AAA  GGC  TCG  GTG  AAA  GAT  TTA  GGT  ATC  AAT  CCG  GAA  TGG  ATT  TCA  AAA     3285
Lys  Gly  Ser  Val  Lys  Asp  Leu  Gly  Ile  Asn  Pro  Glu  Trp  Ile  Ser  Lys
          725                      730                     735

GTT  GAA  AAC  CTT  AAT  GCA  GCT  TTG  AAT  GAA  TTC  AAA  AAT  GGC  AAA  AAT     3333
Val  Glu  Asn  Leu  Asn  Ala  Ala  Leu  Asn  Glu  Phe  Lys  Asn  Gly  Lys  Asn
     740                      745                      750

AAG  GAT  TTC  AGC  AAG  GTA  ACG  CAA  GCA  AAA  AGC  GAC  CAA  GAA  AAT  TCC     3381
Lys  Asp  Phe  Ser  Lys  Val  Thr  Gln  Ala  Lys  Ser  Asp  Gln  Glu  Asn  Ser
755                     760                      765                     770

ATT  AAA  GAT  GTG  ATC  ATC  AAT  CAA  AAG  ATA  ACG  GAT  AAA  GTT  GAT  GAA     3429
Ile  Lys  Asp  Val  Ile  Ile  Asn  Gln  Lys  Ile  Thr  Asp  Lys  Val  Asp  Glu
                    775                      780                     785

CTC  AAT  CAA  GCG  GTA  TCA  GTG  GCT  AAA  ATA  GCG  TGC  GAT  TTC  AGT  GGG     3477
Leu  Asn  Gln  Ala  Val  Ser  Val  Ala  Lys  Ile  Ala  Cys  Asp  Phe  Ser  Gly
               790                      795                     800

GTA  GAG  CAA  GCG  TTA  GCC  GAT  CTC  AAA  AAT  TTC  TCA  AAG  GAG  CAA  TTG     3525
Val  Glu  Gln  Ala  Leu  Ala  Asp  Leu  Lys  Asn  Phe  Ser  Lys  Glu  Gln  Leu
          805                      810                     815

GCT  CAA  CAA  GCT  CAA  AAA  AAT  GAA  AGT  TTC  AAT  GTT  GGA  AAA  TCT  GAA     3573
Ala  Gln  Gln  Ala  Gln  Lys  Asn  Glu  Ser  Phe  Asn  Val  Gly  Lys  Ser  Glu
820                     825                      830

ATA  TAC  CAA  TCC  GTT  AAG  AAT  GGT  GTG  AAC  GGA  ACC  CTA  GTC  GGT  AAT     3621
Ile  Tyr  Gln  Ser  Val  Lys  Asn  Gly  Val  Asn  Gly  Thr  Leu  Val  Gly  Asn
835                     840                      845                     850

GGG  TTA  TCT  GGA  ATA  GAG  GCC  ACA  GGG                                         3648
Gly  Leu  Ser  Gly  Ile  Glu  Ala  Thr  Gly
               855
```

( 2 ) INFORMATION FOR SEQ ID NO:2:

( i ) SEQUENCE CHARACTERISTICS:
        ( A ) LENGTH: 859 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Thr  Asn  Glu  Thr  Ile  Asp  Gln  Gln  Pro  Gln  Thr  Glu  Ala  Ala  Phe
 1                  5                     10                     15

Asn  Pro  Gln  Gln  Phe  Ile  Asn  Asn  Leu  Gln  Val  Ala  Phe  Leu  Lys  Val
               20                      25                     30

Asp  Asn  Ala  Val  Ala  Ser  Tyr  Asp  Pro  Asp  Gln  Lys  Pro  Ile  Val  Asp
          35                      40                     45

Lys  Asn  Asp  Arg  Asp  Asn  Arg  Gln  Ala  Phe  Glu  Gly  Ile  Ser  Gln  Leu
     50                      55                     60

Arg  Glu  Glu  Tyr  Ser  Asn  Lys  Ala  Ile  Lys  Asn  Pro  Thr  Lys  Lys  Asn
 65                     70                      75                     80

Gln  Tyr  Phe  Ser  Asp  Phe  Ile  Asn  Lys  Ser  Asn  Asp  Leu  Ile  Asn  Lys
               85                      90                     95

Asp  Asn  Leu  Ile  Val  Val  Glu  Ser  Ser  Thr  Lys  Ser  Phe  Gln  Lys  Phe
          100                     105                    110

Gly  Asp  Gln  Arg  Tyr  Arg  Ile  Phe  Thr  Ser  Trp  Val  Ser  His  Gln  Asn
     115                     120                    125

Asp  Pro  Ser  Lys  Ile  Asn  Thr  Arg  Cys  Ile  Arg  Asn  Phe  Met  Glu  His
130                     135                     140
```

```
Thr  Ile  Gln  Pro  Pro  Ile  Pro  Asp  Asp  Lys  Glu  Lys  Ala  Glu  Phe  Leu
145                 150                 155                      160

Lys  Ser  Ala  Lys  Gln  Ser  Phe  Ala  Gly  Ile  Ile  Ile  Gly  Asn  Gln  Ile
                    165                 170                      175

Arg  Thr  Asp  Gln  Lys  Phe  Met  Gly  Val  Phe  Asp  Glu  Ser  Leu  Lys  Glu
               180                 185                      190

Arg  Gln  Glu  Ala  Glu  Lys  Asn  Gly  Gly  Pro  Thr  Gly  Gly  Asp  Trp  Leu
          195                      200                 205

Asp  Ile  Phe  Leu  Ser  Phe  Ile  Phe  Asp  Lys  Lys  Gln  Ser  Ser  Asp  Val
          210                 215                 220

Lys  Glu  Ala  Ile  Asn  Gln  Glu  Pro  Leu  Pro  His  Val  Gln  Pro  Asp  Ile
225                      230                 235                      240

Ala  Thr  Ser  Thr  Thr  His  Ile  Gln  Gly  Leu  Pro  Pro  Glu  Ser  Arg  Asp
                    245                 250                      255

Leu  Leu  Asp  Glu  Arg  Gly  Asn  Phe  Ser  Lys  Phe  Thr  Leu  Gly  Asp  Met
               260                 265                      270

Glu  Met  Leu  Asp  Val  Glu  Gly  Val  Ala  Asp  Met  Asp  Pro  Asn  Tyr  Lys
          275                 280                 285

Phe  Asn  Gln  Leu  Leu  Ile  His  Asn  Asn  Thr  Leu  Ser  Val  Leu  Met
290                      295                 300

Gly  Ser  His  Asp  Gly  Ile  Glu  Pro  Glu  Lys  Val  Ser  Leu  Leu  Tyr  Ala
305                      310                 315                      320

Gly  Asn  Gly  Gly  Phe  Gly  Ala  Lys  His  Asp  Trp  Asn  Ala  Thr  Val  Gly
                    325                 330                      335

Tyr  Lys  Asp  Gln  Gln  Gly  Asn  Asn  Val  Ala  Thr  Ile  Ile  Asn  Val  His
               340                 345                      350

Met  Lys  Asn  Gly  Ser  Gly  Leu  Val  Ile  Ala  Gly  Gly  Glu  Lys  Gly  Ile
          355                 360                 365

Asn  Asn  Pro  Ser  Phe  Tyr  Leu  Tyr  Lys  Glu  Asp  Gln  Leu  Thr  Gly  Ser
370                      375                 380

Gln  Arg  Ala  Leu  Ser  Gln  Glu  Glu  Ile  Gln  Asn  Lys  Ile  Asp  Phe  Met
385                 390                 395                      400

Glu  Phe  Leu  Ala  Gln  Asn  Asn  Ala  Lys  Leu  Asp  Ser  Leu  Ser  Glu  Lys
                    405                 410                      415

Glu  Lys  Glu  Lys  Phe  Arg  Asn  Glu  Ile  Lys  Asp  Phe  Gln  Lys  Asp  Ser
               420                 425                      430

Lys  Pro  Tyr  Leu  Asp  Ala  Leu  Gly  Asn  Asp  Arg  Ile  Ala  Phe  Val  Ser
               435                 440                 445

Lys  Lys  Asp  Pro  Lys  His  Ser  Ala  Leu  Ile  Thr  Glu  Phe  Asn  Lys  Gly
     450                 455                 460

Asp  Leu  Ser  Tyr  Thr  Leu  Lys  Val  Met  Gly  Lys  Lys  Gln  Ile  Lys  Ala
465                      470                 475                      480

Leu  Asp  Arg  Glu  Lys  Asn  Val  Thr  Leu  Gln  Gly  Asn  Leu  Lys  His  Asp
               485                 490                      495

Gly  Val  Met  Phe  Val  Asn  Tyr  Ser  Asn  Phe  Lys  Tyr  Thr  Asn  Ala  Ser
          500                 505                      510

Lys  Ser  Pro  Asn  Lys  Gly  Val  Gly  Val  Thr  Asn  Gly  Val  Ser  His  Leu
          515                 520                 525

Glu  Ala  Gly  Phe  Ser  Lys  Val  Ala  Val  Phe  Asn  Leu  Pro  Asn  Leu  Asn
          530                 535                 540

Asn  Leu  Ala  Ile  Thr  Ser  Val  Val  Arg  Arg  Asp  Leu  Glu  Asp  Lys  Leu
545                 550                 555                      560

Ile  Ala  Lys  Gly  Leu  Ser  Pro  Gln  Glu  Ala  Asn  Lys  Leu  Val  Lys  Asp
                    565                 570                      575
```

| | | | | | | | | | | | | | | |
|---|---|---|---|---|---|---|---|---|---|---|---|---|---|---|
| Phe | Leu | Ser | Ser | Asn | Lys | Glu | Leu | Val | Gly | Lys | Ala | Leu | Asn | Phe | Asn |
| | | | 580 | | | | 585 | | | | | 590 | | |
| Lys | Ala | Val | Ala | Glu | Ala | Lys | Asn | Thr | Gly | Asn | Tyr | Asp | Glu | Val | Lys |
| | | 595 | | | | 600 | | | | 605 | | | | |
| Arg | Ala | Gln | Lys | Asp | Leu | Glu | Lys | Ser | Leu | Lys | Lys | Arg | Glu | His | Leu |
| 610 | | | | | 615 | | | | | 620 | | | | |
| Glu | Lys | Asp | Val | Ala | Lys | Asn | Leu | Glu | Ser | Lys | Ser | Gly | Asn | Lys | Asn |
| 625 | | | | | 630 | | | | 635 | | | | | 640 |
| Lys | Met | Glu | Ala | Lys | Ala | Gln | Ala | Asn | Ser | Gln | Lys | Asp | Glu | Ile | Phe |
| | | | | 645 | | | | | 650 | | | | | 655 |
| Ala | Leu | Ile | Asn | Lys | Glu | Ala | Asn | Arg | Asp | Ala | Arg | Ala | Ile | Ala | Tyr |
| | | | 660 | | | | | 665 | | | | 670 | | |
| Ala | Gln | Asn | Leu | Lys | Gly | Ile | Lys | Arg | Glu | Leu | Ser | Asp | Lys | Leu | Glu |
| | | 675 | | | | | 680 | | | | 685 | | | |
| Asn | Ile | Asn | Lys | Asp | Leu | Lys | Asp | Phe | Ser | Lys | Ser | Phe | Asp | Gly | Phe |
| | 690 | | | | | 695 | | | | 700 | | | | |
| Lys | Asn | Gly | Lys | Asn | Lys | Asp | Phe | Ser | Lys | Ala | Glu | Glu | Thr | Leu | Lys |
| 705 | | | | | 710 | | | | 715 | | | | | 720 |
| Ala | Leu | Lys | Gly | Ser | Val | Lys | Asp | Leu | Gly | Ile | Asn | Pro | Glu | Trp | Ile |
| | | | | 725 | | | | 730 | | | | | 735 | |
| Ser | Lys | Val | Glu | Asn | Leu | Asn | Ala | Ala | Leu | Asn | Glu | Phe | Lys | Asn | Gly |
| | | | 740 | | | | 745 | | | | | 750 | | |
| Lys | Asn | Lys | Asp | Phe | Ser | Lys | Val | Thr | Gln | Ala | Lys | Ser | Asp | Gln | Glu |
| | | 755 | | | | | 760 | | | | 765 | | | |
| Asn | Ser | Ile | Lys | Asp | Val | Ile | Ile | Asn | Gln | Lys | Ile | Thr | Asp | Lys | Val |
| | 770 | | | | | 775 | | | | 780 | | | | |
| Asp | Glu | Leu | Asn | Gln | Ala | Val | Ser | Val | Ala | Lys | Ile | Ala | Cys | Asp | Phe |
| 785 | | | | 790 | | | | | 795 | | | | | 800 |
| Ser | Gly | Val | Glu | Gln | Ala | Leu | Ala | Asp | Leu | Lys | Asn | Phe | Ser | Lys | Glu |
| | | | | 805 | | | | 810 | | | | | 815 | |
| Gln | Leu | Ala | Gln | Gln | Ala | Gln | Lys | Asn | Glu | Ser | Phe | Asn | Val | Gly | Lys |
| | | | 820 | | | | 825 | | | | | 830 | | |
| Ser | Glu | Ile | Tyr | Gln | Ser | Val | Lys | Asn | Gly | Val | Asn | Gly | Thr | Leu | Val |
| | | 835 | | | | | 840 | | | | 845 | | | |
| Gly | Asn | Gly | Leu | Ser | Gly | Ile | Glu | Ala | Thr | Gly | | | | | |
| 850 | | | | | | 855 | | | | | | | | |

( 2 ) INFORMATION FOR SEQ ID NO:3:

( i ) SEQUENCE CHARACTERISTICS:
        ( A ) LENGTH: 4821 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1072..4614

( x i ) SEQUENCE DESCRIPTION: SEQ ID NO:3:

| | | | | | |
|---|---|---|---|---|---|
| ATGGGCTGCG | CGTAACGAAA | AACAGTCGCT | TGACCTCTTT | TGATGTCATC | AGAGATTTTC | 60 |
| CAAATATCCG | CTATACCTTT | GACTCCTAGA | GCGCAACCAC | CTACGATCGC | TAGAACAGAA | 120 |
| ATGATCTGAA | CCACCAAAGT | TTTAGTCTCA | GTAATGCCTG | ATGCAGGACT | GTCGAAAGCC | 180 |
| ATTAAAGGAT | TGGCTGCTAT | CGCTAGCCCT | AAAGTTACTA | CAACTTTCTT | GTAGCTGTCA | 240 |

-continued

```
GTGATTCTTG  TAAAAAATTT  CATGCGTTTC  CTTTCAAATT  GAAATCAATC  GTTTGAGTAT    300

ATCAAAAAAA  AGTATTTTTA  TACTATTCAT  ACAAGCGCTA  CTTTATAATT  TAAATCAAAA    360

CCGACGCTTT  TGTTTGACAA  CTGATATAAT  TTAGGAACAA  TAAACCTACT  TGTCCCAACC    420

ATTTTTCTTT  CTCAAGTCAT  CGTAGAATTG  TAGATCTTTA  GGATCTTTGA  TGTATTTTTT    480

AATCGTCTCA  GGTTGAAACC  TAAAAACAAG  CAGAAACAAA  CCCAAGCTGA  TCAGAGTGAG    540

AATAAGCTC   CATTTTAAGC  AACTCCATAA  ACCACTAAAG  AAACTTTTTT  TGAGACTCTC    600

TTTGAAAATC  TGTCCTATTG  ATTTGTTTC   CATTTTGTTT  CCCATGCGGA  TCACAAACGC    660

TTAATTACAA  ATACATACTA  TAATAAGTAT  GGCACACACA  AACCAAACCA  TTTTTAGAAC    720

GCTTCATGCA  CTCACCTTGC  TCCTAACCAT  TTCTCCAACC  ATCTTTAGCG  TTGCATTTGA    780

TTTCTTCAAA  AAGGCTCATT  TCTTAGTTTC  TTTTATTCTT  AAAATTTTTC  CATTCTAGCA    840

AATTTTTGTT  AATTGTGGGT  AAAAATGTGA  ATCGTTCCTA  GCTTTAGAC   GCTTGCAACG    900

ATCGGACTTT  TTTCAATATT  AATGAAAAAA  TGCCAAATAT  TCTAAATATT  GTGGTATAGT    960

GATAACGTTC  AAAGACACGA  ATTGCATACT  CAAAGTGTGT  AGTAGTTTTT  AGCGGTCTTT   1020

GATACCAATA  AGATACCGAT  AGGTATGAAA  CTAGGTATAG  AAGGAGAAAC  A ATG ACT   1077
                                                            Met Thr
                                                              1
```

| | | | | | | | | | | | | | | | |
|---|---|---|---|---|---|---|---|---|---|---|---|---|---|---|---|
| AAC | GAA | ACT | ATT | GAC | CAA | CAA | CCA | CAA | ACC | GAA | GCG | GCT | TTT | AAC | CCG |
| Asn | Glu | Thr | Ile | Asp | Gln | Gln | Pro | Gln | Thr | Glu | Ala | Ala | Phe | Asn | Pro |
| | | 5 | | | | | 10 | | | | | 15 | | | |

1125

| CAG | CAA | TTT | ATC | AAT | AAT | CTT | CAA | GTA | GCT | TTT | CTT | AAA | GTT | GAT | AAC |
|---|---|---|---|---|---|---|---|---|---|---|---|---|---|---|---|
| Gln | Gln | Phe | Ile | Asn | Asn | Leu | Gln | Val | Ala | Phe | Leu | Lys | Val | Asp | Asn |
| | | 20 | | | | | 25 | | | | | 30 | | | |

1173

| GCT | GTC | GCT | TCA | TAC | GAT | CCT | GAT | CAA | AAA | CCA | ATC | GTT | GAT | AAG | AAC |
|---|---|---|---|---|---|---|---|---|---|---|---|---|---|---|---|
| Ala | Val | Ala | Ser | Tyr | Asp | Pro | Asp | Gln | Lys | Pro | Ile | Val | Asp | Lys | Asn |
| 35 | | | | 40 | | | | | 45 | | | | | 50 | |

1221

| GAT | AGG | GAT | AAC | AGG | CAA | GCT | TTT | GAG | GGA | ATC | TCG | CAA | TTA | AGG | GAA |
|---|---|---|---|---|---|---|---|---|---|---|---|---|---|---|---|
| Asp | Arg | Asp | Asn | Arg | Gln | Ala | Phe | Glu | Gly | Ile | Ser | Gln | Leu | Arg | Glu |
| | | | | 55 | | | | | 60 | | | | | 65 | |

1269

| GAA | TAC | TCC | AAT | AAA | GCG | ATC | AAA | AAT | CCT | ACC | AAA | AAG | AAT | CAG | TAT |
|---|---|---|---|---|---|---|---|---|---|---|---|---|---|---|---|
| Glu | Tyr | Ser | Asn | Lys | Ala | Ile | Lys | Asn | Pro | Thr | Lys | Lys | Asn | Gln | Tyr |
| | | | 70 | | | | | 75 | | | | | 80 | | |

1317

| TTT | TCA | GAC | TTT | ATC | AAT | AAG | AGC | AAT | GAT | TTA | ATC | AAC | AAA | GAC | AAT |
|---|---|---|---|---|---|---|---|---|---|---|---|---|---|---|---|
| Phe | Ser | Asp | Phe | Ile | Asn | Lys | Ser | Asn | Asp | Leu | Ile | Asn | Lys | Asp | Asn |
| | | | 85 | | | | | 90 | | | | | 95 | | |

1365

| CTC | ATT | GTC | GTG | GAA | TCT | TCC | ACA | AAG | AGC | TTT | CAG | AAA | TTT | GGG | GAT |
|---|---|---|---|---|---|---|---|---|---|---|---|---|---|---|---|
| Leu | Ile | Val | Val | Glu | Ser | Ser | Thr | Lys | Ser | Phe | Gln | Lys | Phe | Gly | Asp |
| | | | 100 | | | | | 105 | | | | | 110 | | |

1413

| CAG | CGT | TAC | CGA | ATT | TTC | ACA | AGT | TGG | GTG | TCC | CAT | CAA | AAC | GAT | CCG |
|---|---|---|---|---|---|---|---|---|---|---|---|---|---|---|---|
| Gln | Arg | Tyr | Arg | Ile | Phe | Thr | Ser | Trp | Val | Ser | His | Gln | Asn | Asp | Pro |
| 115 | | | | | 120 | | | | | 125 | | | | | 130 |

1461

| TCT | AAA | ATC | AAC | ACC | CGA | TGC | ATC | CGA | AAT | TTT | ATG | GAA | CAT | ACC | ATA |
|---|---|---|---|---|---|---|---|---|---|---|---|---|---|---|---|
| Ser | Lys | Ile | Asn | Thr | Arg | Cys | Ile | Arg | Asn | Phe | Met | Glu | His | Thr | Ile |
| | | | | 135 | | | | | 140 | | | | | 145 | |

1509

| CAA | CCC | CCT | ATC | CCT | GAT | GAC | AAA | GAA | AAA | GCA | GAG | TTT | TTG | AAA | TCT |
|---|---|---|---|---|---|---|---|---|---|---|---|---|---|---|---|
| Gln | Pro | Pro | Ile | Pro | Asp | Asp | Lys | Glu | Lys | Ala | Glu | Phe | Leu | Lys | Ser |
| | | | | 150 | | | | | 155 | | | | | 160 | |

1557

| GCC | AAA | CAA | TCT | TTT | GCA | GGA | ATC | ATC | ATA | GGG | AAT | CAA | ATC | CGA | ACG |
|---|---|---|---|---|---|---|---|---|---|---|---|---|---|---|---|
| Ala | Lys | Gln | Ser | Phe | Ala | Gly | Ile | Ile | Ile | Gly | Asn | Gln | Ile | Arg | Thr |
| | | 165 | | | | | 170 | | | | | 175 | | | |

1605

| GAT | CAA | AAA | TTC | ATG | GGC | GTG | TTT | GAT | GAA | TCC | TTG | AAA | GAA | AGG | CAA |
|---|---|---|---|---|---|---|---|---|---|---|---|---|---|---|---|
| Asp | Gln | Lys | Phe | Met | Gly | Val | Phe | Asp | Glu | Ser | Leu | Lys | Glu | Arg | Gln |
| | | 180 | | | | | 185 | | | | | 190 | | | |

1653

| GAA | GCA | GAA | AAA | AAT | GGA | GGG | CCT | ACT | GGT | GGG | GAT | TGG | TTG | GAT | ATT |
|---|---|---|---|---|---|---|---|---|---|---|---|---|---|---|---|
| Glu | Ala | Glu | Lys | Asn | Gly | Gly | Pro | Thr | Gly | Gly | Asp | Trp | Leu | Asp | Ile |

1701

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 195 |     |     |     |     | 200 |     |     |     |     | 205 |     |     |     |     | 210 |      |
| TTT | TTA | TCA | TTT | ATA | TTT | GAC | AAA | AAA | CAA | TCT | TCT | GAT | GTC | AAA | GAA | 1749 |
| Phe | Leu | Ser | Phe | Ile | Phe | Asp | Lys | Lys | Gln | Ser | Ser | Asp | Val | Lys | Glu |      |
|     |     |     |     | 215 |     |     |     |     | 220 |     |     |     |     | 225 |     |      |
| GCA | ATC | AAT | CAA | GAA | CCA | CTT | CCT | CAT | GTC | CAA | CCA | GAT | ATA | GCC | ACT | 1797 |
| Ala | Ile | Asn | Gln | Glu | Pro | Leu | Pro | His | Val | Gln | Pro | Asp | Ile | Ala | Thr |      |
|     |     |     | 230 |     |     |     |     | 235 |     |     |     |     | 240 |     |     |      |
| AGC | ACC | ACT | CAC | ATA | CAA | GGC | TTA | CCG | CCT | GAA | TCT | AGG | GAT | TTG | CTT | 1845 |
| Ser | Thr | Thr | His | Ile | Gln | Gly | Leu | Pro | Pro | Glu | Ser | Arg | Asp | Leu | Leu |      |
|     |     | 245 |     |     |     |     | 250 |     |     |     |     | 255 |     |     |     |      |
| GAT | GAA | AGG | GGT | AAT | TTT | TCT | AAA | TTC | ACT | CTT | GGC | GAT | ATG | GAA | ATG | 1893 |
| Asp | Glu | Arg | Gly | Asn | Phe | Ser | Lys | Phe | Thr | Leu | Gly | Asp | Met | Glu | Met |      |
|     | 260 |     |     |     |     | 265 |     |     |     |     | 270 |     |     |     |     |      |
| TTA | GAT | GTT | GAG | GGC | GTC | GCC | GAC | ATG | GAT | CCC | AAT | TAC | AAG | TTC | AAT | 1941 |
| Leu | Asp | Val | Glu | Gly | Val | Ala | Asp | Met | Asp | Pro | Asn | Tyr | Lys | Phe | Asn |      |
| 275 |     |     |     | 280 |     |     |     |     | 285 |     |     |     |     |     | 290 |      |
| CAA | TTA | TTG | ATT | CAC | AAT | AAC | ACT | CTG | TCT | TCT | GTG | TTA | ATG | GGG | AGT | 1989 |
| Gln | Leu | Leu | Ile | His | Asn | Asn | Thr | Leu | Ser | Ser | Val | Leu | Met | Gly | Ser |      |
|     |     |     |     | 295 |     |     |     | 300 |     |     |     |     | 305 |     |     |      |
| CAT | GAT | GGC | ATA | GAA | CCT | GAA | AAA | GTT | TCA | TTA | TTG | TAT | GCG | GGC | AAT | 2037 |
| His | Asp | Gly | Ile | Glu | Pro | Glu | Lys | Val | Ser | Leu | Leu | Tyr | Ala | Gly | Asn |      |
|     |     |     | 310 |     |     |     |     | 315 |     |     |     |     | 320 |     |     |      |
| GGT | GGT | TTT | GGA | GCC | AAG | CAC | GAT | TGG | AAC | GCC | ACC | GTT | GGT | TAT | AAA | 2085 |
| Gly | Gly | Phe | Gly | Ala | Lys | His | Asp | Trp | Asn | Ala | Thr | Val | Gly | Tyr | Lys |      |
|     |     | 325 |     |     |     |     | 330 |     |     |     |     | 335 |     |     |     |      |
| GAC | CAA | CAA | GGT | AAC | AAT | GTG | GCT | ACA | ATA | ATT | AAT | GTG | CAT | ATG | AAA | 2133 |
| Asp | Gln | Gln | Gly | Asn | Asn | Val | Ala | Thr | Ile | Ile | Asn | Val | His | Met | Lys |      |
|     | 340 |     |     |     |     | 345 |     |     |     |     | 350 |     |     |     |     |      |
| AAC | GGC | AGT | GGC | TTA | GTC | ATA | GCA | GGT | GGT | GAG | AAA | GGG | ATT | AAC | AAC | 2181 |
| Asn | Gly | Ser | Gly | Leu | Val | Ile | Ala | Gly | Gly | Glu | Lys | Gly | Ile | Asn | Asn |      |
| 355 |     |     |     |     | 360 |     |     |     |     | 365 |     |     |     |     | 370 |      |
| CCT | AGT | TTT | TAT | CTC | TAC | AAA | GAA | GAC | CAA | CTC | ACA | GGC | TCA | CAA | CGA | 2229 |
| Pro | Ser | Phe | Tyr | Leu | Tyr | Lys | Glu | Asp | Gln | Leu | Thr | Gly | Ser | Gln | Arg |      |
|     |     |     |     | 375 |     |     |     | 380 |     |     |     |     | 385 |     |     |      |
| GCA | TTG | AGT | CAA | GAA | GAG | ATC | CAA | AAC | AAA | ATA | GAT | TTC | ATG | GAA | TTT | 2277 |
| Ala | Leu | Ser | Gln | Glu | Glu | Ile | Gln | Asn | Lys | Ile | Asp | Phe | Met | Glu | Phe |      |
|     |     |     | 390 |     |     |     |     | 395 |     |     |     |     | 400 |     |     |      |
| CTT | GCA | CAA | AAC | AAT | GCT | AAA | TTA | GAC | AGC | TTG | AGC | GAG | AAA | GAG | AAA | 2325 |
| Leu | Ala | Gln | Asn | Asn | Ala | Lys | Leu | Asp | Ser | Leu | Ser | Glu | Lys | Glu | Lys |      |
|     |     | 405 |     |     |     |     | 410 |     |     |     |     | 415 |     |     |     |      |
| GAA | AAA | TTC | CGA | AAT | GAG | ATT | AAG | GAT | TTC | CAA | AAA | GAC | TCT | AAG | CCT | 2373 |
| Glu | Lys | Phe | Arg | Asn | Glu | Ile | Lys | Asp | Phe | Gln | Lys | Asp | Ser | Lys | Pro |      |
|     | 420 |     |     |     |     | 425 |     |     |     |     | 430 |     |     |     |     |      |
| TAT | TTA | GAC | GCC | CTA | GGG | AAT | GAT | CGT | ATT | GCT | TTT | GTT | TCT | AAA | AAA | 2421 |
| Tyr | Leu | Asp | Ala | Leu | Gly | Asn | Asp | Arg | Ile | Ala | Phe | Val | Ser | Lys | Lys |      |
| 435 |     |     |     |     | 440 |     |     |     |     | 445 |     |     |     |     | 450 |      |
| GAC | CCA | AAA | CAT | TCA | GCT | TTA | ATT | ACT | GAG | TTT | AAT | AAG | GGG | GAT | TTG | 2469 |
| Asp | Pro | Lys | His | Ser | Ala | Leu | Ile | Thr | Glu | Phe | Asn | Lys | Gly | Asp | Leu |      |
|     |     |     |     | 455 |     |     |     | 460 |     |     |     |     | 465 |     |     |      |
| AGC | TAC | ACT | CTC | AAA | GTT | ATG | GGA | AAA | AAG | CAG | ATA | AAG | GCT | TTA | GAT | 2517 |
| Ser | Tyr | Thr | Leu | Lys | Val | Met | Gly | Lys | Lys | Gln | Ile | Lys | Ala | Leu | Asp |      |
|     |     |     | 470 |     |     |     |     | 475 |     |     |     |     | 480 |     |     |      |
| AGG | GAG | AAA | AAT | GTC | ACT | CTT | CAA | GGT | AAC | CTA | AAA | CAT | GAT | GGC | GTG | 2565 |
| Arg | Glu | Lys | Asn | Val | Thr | Leu | Gln | Gly | Asn | Leu | Lys | His | Asp | Gly | Val |      |
|     |     | 485 |     |     |     |     | 490 |     |     |     |     | 495 |     |     |     |      |
| ATG | TTT | GTT | AAT | TAT | TCT | AAT | TTC | AAA | TAC | ACC | AAC | GCC | TCC | AAG | AGT | 2613 |
| Met | Phe | Val | Asn | Tyr | Ser | Asn | Phe | Lys | Tyr | Thr | Asn | Ala | Ser | Lys | Ser |      |
|     | 500 |     |     |     |     | 505 |     |     |     |     | 510 |     |     |     |     |      |
| CCC | AAT | AAG | GGT | GTA | GGC | GTT | ACG | AAT | GGC | GTT | TCC | CAT | TTA | GAA | GCA | 2661 |
| Pro | Asn | Lys | Gly | Val | Gly | Val | Thr | Asn | Gly | Val | Ser | His | Leu | Glu | Ala |      |

-continued

| | | | | | | | | | | | | | | | | |
|---|---|---|---|---|---|---|---|---|---|---|---|---|---|---|---|---|
| 515 | | | | | 520 | | | | | 525 | | | | | 530 | |
| GGC | TTT | AGC | AAG | GTG | GCT | GTC | TTT | AAT | TTG | CCT | AAT | TTA | AAT | AAT | CTC | 2709 |
| Gly | Phe | Ser | Lys | Val | Ala | Val | Phe | Asn | Leu | Pro | Asn | Leu | Asn | Asn | Leu | |
| | | | 535 | | | | | 540 | | | | | 545 | | | |
| GCT | ATC | ACT | AGT | GTC | GTA | AGG | CGG | GAT | TTA | GAG | GAT | AAA | CTA | ATC | GCT | 2757 |
| Ala | Ile | Thr | Ser | Val | Val | Arg | Arg | Asp | Leu | Glu | Asp | Lys | Leu | Ile | Ala | |
| | | | 550 | | | | | 555 | | | | | 560 | | | |
| AAA | GGA | TTG | TCC | CCA | CAA | GAA | GCT | AAT | AAG | CTT | GTC | AAA | GAT | TTT | TTG | 2805 |
| Lys | Gly | Leu | Ser | Pro | Gln | Glu | Ala | Asn | Lys | Leu | Val | Lys | Asp | Phe | Leu | |
| | | 565 | | | | | 570 | | | | | 575 | | | | |
| AGT | AGC | AAC | AAA | GAA | TTG | GTT | GGA | AAA | GCT | TTA | AAC | TTC | AAT | AAA | GCT | 2853 |
| Ser | Ser | Asn | Lys | Glu | Leu | Val | Gly | Lys | Ala | Leu | Asn | Phe | Asn | Lys | Ala | |
| | 580 | | | | | 585 | | | | | 590 | | | | | |
| GTA | GCT | GAA | GCT | AAA | AAC | ACA | GGC | AAC | TAT | GAC | GAG | GTG | AAA | CGA | GCT | 2901 |
| Val | Ala | Glu | Ala | Lys | Asn | Thr | Gly | Asn | Tyr | Asp | Glu | Val | Lys | Arg | Ala | |
| 595 | | | | | 600 | | | | | 605 | | | | | 610 | |
| CAG | AAA | GAT | CTT | GAA | AAA | TCT | CTA | AAG | AAA | CGA | GAG | CAT | TTG | GAG | AAG | 2949 |
| Gln | Lys | Asp | Leu | Glu | Lys | Ser | Leu | Lys | Lys | Arg | Glu | His | Leu | Glu | Lys | |
| | | | | 615 | | | | | 620 | | | | | 625 | | |
| GAT | GTA | GCG | AAA | AAT | TTG | GAG | AGC | AAA | AGC | GGC | AAC | AAA | AAT | AAA | ATG | 2997 |
| Asp | Val | Ala | Lys | Asn | Leu | Glu | Ser | Lys | Ser | Gly | Asn | Lys | Asn | Lys | Met | |
| | | | 630 | | | | | 635 | | | | | 640 | | | |
| GAA | GCA | AAA | GCT | CAA | GCT | AAC | AGC | CAA | AAA | GAT | GAG | ATT | TTT | GCG | TTG | 3045 |
| Glu | Ala | Lys | Ala | Gln | Ala | Asn | Ser | Gln | Lys | Asp | Glu | Ile | Phe | Ala | Leu | |
| | | 645 | | | | | 650 | | | | | 655 | | | | |
| ATC | AAT | AAA | GAG | GCT | AAT | AGA | GAC | GCA | AGA | GCA | ATC | GCT | TAC | GCT | CAA | 3093 |
| Ile | Asn | Lys | Glu | Ala | Asn | Arg | Asp | Ala | Arg | Ala | Ile | Ala | Tyr | Ala | Gln | |
| | | 660 | | | | | 665 | | | | | 670 | | | | |
| AAT | CTT | AAA | GGC | ATC | AAA | AGG | GAA | TTG | TCT | GAT | AAA | CTT | GAA | AAT | ATC | 3141 |
| Asn | Leu | Lys | Gly | Ile | Lys | Arg | Glu | Leu | Ser | Asp | Lys | Leu | Glu | Asn | Ile | |
| 675 | | | | | 680 | | | | | 685 | | | | | 690 | |
| AAC | AAG | GAT | TTG | AAA | GAC | TTT | AGT | AAA | TCT | TTT | GAT | GGA | TTC | AAA | AAT | 3189 |
| Asn | Lys | Asp | Leu | Lys | Asp | Phe | Ser | Lys | Ser | Phe | Asp | Gly | Phe | Lys | Asn | |
| | | | | 695 | | | | | 700 | | | | | 705 | | |
| GGC | AAA | AAT | AAG | GAT | TTC | AGC | AAG | GCA | GAA | GAA | ACG | CTA | AAA | GCC | CTT | 3237 |
| Gly | Lys | Asn | Lys | Asp | Phe | Ser | Lys | Ala | Glu | Glu | Thr | Leu | Lys | Ala | Leu | |
| | | | 710 | | | | | 715 | | | | | 720 | | | |
| AAA | GGC | TCG | GTG | AAA | GAT | TTA | GGT | ATC | AAT | CCG | GAA | TGG | ATT | TCA | AAA | 3285 |
| Lys | Gly | Ser | Val | Lys | Asp | Leu | Gly | Ile | Asn | Pro | Glu | Trp | Ile | Ser | Lys | |
| | | 725 | | | | | 730 | | | | | 735 | | | | |
| GTT | GAA | AAC | CTT | AAT | GCA | GCT | TTG | AAT | GAA | TTC | AAA | AAT | GGC | AAA | AAT | 3333 |
| Val | Glu | Asn | Leu | Asn | Ala | Ala | Leu | Asn | Glu | Phe | Lys | Asn | Gly | Lys | Asn | |
| | | 740 | | | | | 745 | | | | | 750 | | | | |
| AAG | GAT | TTC | AGC | AAG | GTA | ACG | CAA | GCA | AAA | AGC | GAC | CAA | GAA | AAT | TCC | 3381 |
| Lys | Asp | Phe | Ser | Lys | Val | Thr | Gln | Ala | Lys | Ser | Asp | Gln | Glu | Asn | Ser | |
| 755 | | | | | 760 | | | | | 765 | | | | | 770 | |
| ATT | AAA | GAT | GTG | ATC | ATC | AAT | CAA | AAG | ATA | ACG | GAT | AAA | GTT | GAT | GAA | 3429 |
| Ile | Lys | Asp | Val | Ile | Ile | Asn | Gln | Lys | Ile | Thr | Asp | Lys | Val | Asp | Glu | |
| | | | | 775 | | | | | 780 | | | | | 785 | | |
| CTC | AAT | CAA | GCG | GTA | TCA | GTG | GCT | AAA | ATA | GCG | TGC | GAT | TTC | AGT | GGG | 3477 |
| Leu | Asn | Gln | Ala | Val | Ser | Val | Ala | Lys | Ile | Ala | Cys | Asp | Phe | Ser | Gly | |
| | | | 790 | | | | | 795 | | | | | 800 | | | |
| GTA | GAG | CAA | GCG | TTA | GCC | GAT | CTC | AAA | AAT | TTC | TCA | AAG | GAG | CAA | TTG | 3525 |
| Val | Glu | Gln | Ala | Leu | Ala | Asp | Leu | Lys | Asn | Phe | Ser | Lys | Glu | Gln | Leu | |
| | | 805 | | | | | 810 | | | | | 815 | | | | |
| GCT | CAA | CAA | GCT | CAA | AAA | AAT | GAA | AGT | TTC | AAT | GTT | GGA | AAA | TCT | GAA | 3573 |
| Ala | Gln | Gln | Ala | Gln | Lys | Asn | Glu | Ser | Phe | Asn | Val | Gly | Lys | Ser | Glu | |
| | 820 | | | | | 825 | | | | | 830 | | | | | |
| ATA | TAC | CAA | TCC | GTT | AAG | AAT | GGT | GTG | AAC | GGA | ACC | CTA | GTC | GGT | AAT | 3621 |
| Ile | Tyr | Gln | Ser | Val | Lys | Asn | Gly | Val | Asn | Gly | Thr | Leu | Val | Gly | Asn | |

-continued

```
           835                         840                         845                         850
GGG  TTA  TCT  GGA  ATA  GAG  GCC  ACA  GCT  CTC  GCC  AAA  AAT  TTT  TCG  GAT            3669
Gly  Leu  Ser  Gly  Ile  Glu  Ala  Thr  Ala  Leu  Ala  Lys  Asn  Phe  Ser  Asp
                    855                         860                         865

ATC  AAG  AAA  GAA  TTG  AAT  GAG  AAA  TTT  AAA  AAT  TTC  AAT  AAC  AAT  AAC            3717
Ile  Lys  Lys  Glu  Leu  Asn  Glu  Lys  Phe  Lys  Asn  Phe  Asn  Asn  Asn  Asn
                    870                         875                         880

AAT  AAT  GGT  CTC  AAA  AAC  GGC  GGA  GAA  CCC  ATT  TAT  GCT  CAA  GTT  AAT            3765
Asn  Asn  Gly  Leu  Lys  Asn  Gly  Gly  Glu  Pro  Ile  Tyr  Ala  Gln  Val  Asn
                    885                         890                         895

AAA  AAG  AAA  ACA  GGA  CAA  GTA  GCT  AGC  CCT  GAA  GAA  CCC  ATT  TAT  GCT            3813
Lys  Lys  Lys  Thr  Gly  Gln  Val  Ala  Ser  Pro  Glu  Glu  Pro  Ile  Tyr  Ala
900                           905                         910

CAA  GTT  GCT  AAA  AAG  GTA  ACT  AAA  AAA  ATT  GAC  CAA  CTC  AAT  CAA  GCA            3861
Gln  Val  Ala  Lys  Lys  Val  Thr  Lys  Lys  Ile  Asp  Gln  Leu  Asn  Gln  Ala
915                           920                         925                         930

GCG  ACA  AGT  GGT  TTC  GGT  GGT  GTA  GGG  CAA  GCG  GGC  TTC  CCT  TTG  AAA            3909
Ala  Thr  Ser  Gly  Phe  Gly  Gly  Val  Gly  Gln  Ala  Gly  Phe  Pro  Leu  Lys
                    935                         940                         945

AGG  CAT  GAT  AAA  GTT  GAA  GAT  CTC  AGT  AAG  GTA  GGG  CGA  TCA  GTT  AGC            3957
Arg  His  Asp  Lys  Val  Glu  Asp  Leu  Ser  Lys  Val  Gly  Arg  Ser  Val  Ser
                    950                         955                         960

CCT  GAA  CCC  ATT  TAT  GCT  ACA  ATT  GAT  GAT  CTC  GGT  GGG  TCT  TTC  CCT            4005
Pro  Glu  Pro  Ile  Tyr  Ala  Thr  Ile  Asp  Asp  Leu  Gly  Gly  Ser  Phe  Pro
                    965                         970                         975

TTG  AAA  AGG  CAT  GAT  AAA  GTT  GAT  GAT  CTC  AGT  AAG  GTA  GGG  CTT  TCA            4053
Leu  Lys  Arg  His  Asp  Lys  Val  Asp  Asp  Leu  Ser  Lys  Val  Gly  Leu  Ser
980                           985                         990

AGG  AAT  CAA  GAA  TTG  ACT  CAG  AAA  ATT  GAC  AAT  CTC  AGT  CAA  GCG  GTA            4101
Arg  Asn  Gln  Glu  Leu  Thr  Gln  Lys  Ile  Asp  Asn  Leu  Ser  Gln  Ala  Val
995                           1000                        1005                        1010

TCA  GAA  GCT  AAA  GCA  GGT  TTT  TTT  GGC  AAT  CTA  GAA  CAA  ACG  ATA  GAC            4149
Ser  Glu  Ala  Lys  Ala  Gly  Phe  Phe  Gly  Asn  Leu  Glu  Gln  Thr  Ile  Asp
                    1015                        1020                        1025

AAG  CTC  AAA  GAT  TTT  ACA  AAA  AAC  AAT  CCT  GTG  AAT  CTA  TGG  GCT  GAA            4197
Lys  Leu  Lys  Asp  Phe  Thr  Lys  Asn  Asn  Pro  Val  Asn  Leu  Trp  Ala  Glu
                    1030                        1035                        1040

AGC  GCA  AAA  AAA  GTG  CCT  GCT  AGT  TTG  TCA  GCG  AAA  CTA  GAC  AAT  TAC            4245
Ser  Ala  Lys  Lys  Val  Pro  Ala  Ser  Leu  Ser  Ala  Lys  Leu  Asp  Asn  Tyr
                    1045                        1050                        1055

GCT  ACT  AAC  AGC  CAC  ACA  CGC  ATT  AAT  AGC  AAT  ATC  CAA  AAT  GGA  GCG            4293
Ala  Thr  Asn  Ser  His  Thr  Arg  Ile  Asn  Ser  Asn  Ile  Gln  Asn  Gly  Ala
                    1060                        1065                        1070

ATC  AAT  GAA  AAA  GCG  ACC  GGC  ACT  GAA  CGG  CAA  AAA  AAC  CCT  GAG  TGG            4341
Ile  Asn  Glu  Lys  Ala  Thr  Gly  Thr  Glu  Arg  Gln  Lys  Asn  Pro  Glu  Trp
1075                          1080                        1085                        1090

CTC  AAA  CTC  GTG  AAT  GAT  AAG  ATC  GTT  GCG  CAT  AAT  GTG  GGA  AGC  GTT            4389
Leu  Lys  Leu  Val  Asn  Asp  Lys  Ile  Val  Ala  His  Asn  Val  Gly  Ser  Val
                    1095                        1100                        1105

CCT  TTG  TCA  GAG  TAT  GAT  AAC  ATT  GGA  TTC  AGC  CAA  AAG  AAT  ATG  AAG            4437
Pro  Leu  Ser  Glu  Tyr  Asp  Asn  Ile  Gly  Phe  Ser  Gln  Lys  Asn  Met  Lys
                    1110                        1115                        1120

GAT  TAT  TCT  GAT  TCG  TTC  AAG  TTT  TCC  ACC  AAG  TTG  AAC  AAT  GCC  GTA            4485
Asp  Tyr  Ser  Asp  Ser  Phe  Lys  Phe  Ser  Thr  Lys  Leu  Asn  Asn  Ala  Val
                    1125                        1130                        1135

AAA  GAC  ATT  AAG  TCT  GGC  TTT  ACG  CAA  TTT  TTA  GCC  AAT  GCA  TTT  TCT            4533
Lys  Asp  Ile  Lys  Ser  Gly  Phe  Thr  Gln  Phe  Leu  Ala  Asn  Ala  Phe  Ser
1140                          1145                        1150

ACA  GGA  TAT  TAC  TCC  ATG  GCG  AGA  GAA  AAT  GCG  GAG  CAT  GGA  ATC  AAA            4581
Thr  Gly  Tyr  Tyr  Ser  Met  Ala  Arg  Glu  Asn  Ala  Glu  His  Gly  Ile  Lys
```

-continued

```
      1155                1160                1165                1170
AAT GCT AAT ACA AAA GGT GGT TTC CAA AAA TCT TAAAGGATTA AGGAACACCA       4634
Asn Ala Asn Thr Lys Gly Gly Phe Gln Lys Ser
                1175                1180

AAAACGCAAA AACCACCTTG CTAAAAGCAA GGGGTTTTTT AACTTAAAAT ATCCCGACAG       4694

ACACTAACGA AAGGCTTTGT TCTTTAAAGT CTGCATAGAT ATTTCCTACC CCAAAAAGAC       4754

TTAACCCTTT GCTTAAAATT AAATTTGATT GTGCTAGTGG GTTCGTGCTT TATAGTGCGG       4814

AATTGGG                                                                 4821
```

( 2 ) INFORMATION FOR SEQ ID NO:4:

( i ) SEQUENCE CHARACTERISTICS:
        ( A ) LENGTH: 1181 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Thr Asn Glu Thr Ile Asp Gln Gln Pro Gln Thr Glu Ala Ala Phe
 1               5                  10                 15

Asn Pro Gln Gln Phe Ile Asn Asn Leu Gln Val Ala Phe Leu Lys Val
                20                 25                 30

Asp Asn Ala Val Ala Ser Tyr Asp Pro Asp Gln Lys Pro Ile Val Asp
            35                  40                 45

Lys Asn Asp Arg Asp Asn Arg Gln Ala Phe Glu Gly Ile Ser Gln Leu
         50                 55                 60

Arg Glu Glu Tyr Ser Asn Lys Ala Ile Lys Asn Pro Thr Lys Lys Asn
 65                  70                 75                 80

Gln Tyr Phe Ser Asp Phe Ile Asn Lys Ser Asn Asp Leu Ile Asn Lys
                 85                 90                 95

Asp Asn Leu Ile Val Val Glu Ser Ser Thr Lys Ser Phe Gln Lys Phe
           100                 105                110

Gly Asp Gln Arg Tyr Arg Ile Phe Thr Ser Trp Val Ser His Gln Asn
         115                 120                125

Asp Pro Ser Lys Ile Asn Thr Arg Cys Ile Arg Asn Phe Met Glu His
     130                 135                 140

Thr Ile Gln Pro Pro Ile Pro Asp Asp Lys Glu Lys Ala Glu Phe Leu
145                 150                 155                160

Lys Ser Ala Lys Gln Ser Phe Ala Gly Ile Ile Gly Asn Gln Ile
                 165                 170                175

Arg Thr Asp Gln Lys Phe Met Gly Val Phe Asp Glu Ser Leu Lys Glu
             180                 185                190

Arg Gln Glu Ala Glu Lys Asn Gly Gly Pro Thr Gly Gly Asp Trp Leu
         195                 200                 205

Asp Ile Phe Leu Ser Phe Ile Phe Asp Lys Lys Gln Ser Ser Asp Val
     210                 215                 220

Lys Glu Ala Ile Asn Gln Glu Pro Leu Pro His Val Gln Pro Asp Ile
225                 230                 235                240

Ala Thr Ser Thr Thr His Ile Gln Gly Leu Pro Pro Glu Ser Arg Asp
                 245                 250                255

Leu Leu Asp Glu Arg Gly Asn Phe Ser Lys Phe Thr Leu Gly Asp Met
             260                 265                270

Glu Met Leu Asp Val Glu Gly Val Ala Asp Met Asp Pro Asn Tyr Lys
         275                 280                 285
```

-continued

| | | | | | | | | | | | | | | | |
|---|---|---|---|---|---|---|---|---|---|---|---|---|---|---|---|
| Phe | Asn | Gln | Leu | Leu | Ile | His | Asn | Asn | Thr | Leu | Ser | Ser | Val | Leu | Met |
| | 290 | | | | 295 | | | | | 300 | | | | | |
| Gly | Ser | His | Asp | Gly | Ile | Glu | Pro | Glu | Lys | Val | Ser | Leu | Leu | Tyr | Ala |
| 305 | | | | | 310 | | | | 315 | | | | | | 320 |
| Gly | Asn | Gly | Gly | Phe | Gly | Ala | Lys | His | Asp | Trp | Asn | Ala | Thr | Val | Gly |
| | | | | 325 | | | | | 330 | | | | | 335 | |
| Tyr | Lys | Asp | Gln | Gln | Gly | Asn | Asn | Val | Ala | Thr | Ile | Ile | Asn | Val | His |
| | | | 340 | | | | | 345 | | | | | 350 | | |
| Met | Lys | Asn | Gly | Ser | Gly | Leu | Val | Ile | Ala | Gly | Gly | Glu | Lys | Gly | Ile |
| | | 355 | | | | | 360 | | | | | 365 | | | |
| Asn | Asn | Pro | Ser | Phe | Tyr | Leu | Tyr | Lys | Glu | Asp | Gln | Leu | Thr | Gly | Ser |
| | 370 | | | | | 375 | | | | | 380 | | | | |
| Gln | Arg | Ala | Leu | Ser | Gln | Glu | Glu | Ile | Gln | Asn | Lys | Ile | Asp | Phe | Met |
| 385 | | | | | 390 | | | | | 395 | | | | | 400 |
| Glu | Phe | Leu | Ala | Gln | Asn | Asn | Ala | Lys | Leu | Asp | Ser | Leu | Ser | Glu | Lys |
| | | | | 405 | | | | | 410 | | | | | 415 | |
| Glu | Lys | Glu | Lys | Phe | Arg | Asn | Glu | Ile | Lys | Asp | Phe | Gln | Lys | Asp | Ser |
| | | | 420 | | | | | 425 | | | | | 430 | | |
| Lys | Pro | Tyr | Leu | Asp | Ala | Leu | Gly | Asn | Asp | Arg | Ile | Ala | Phe | Val | Ser |
| | | 435 | | | | | 440 | | | | | 445 | | | |
| Lys | Lys | Asp | Pro | Lys | His | Ser | Ala | Leu | Ile | Thr | Glu | Phe | Asn | Lys | Gly |
| 450 | | | | | 455 | | | | | 460 | | | | | |
| Asp | Leu | Ser | Tyr | Thr | Leu | Lys | Val | Met | Gly | Lys | Lys | Gln | Ile | Lys | Ala |
| 465 | | | | | 470 | | | | 475 | | | | | | 480 |
| Leu | Asp | Arg | Glu | Lys | Asn | Val | Thr | Leu | Gln | Gly | Asn | Leu | Lys | His | Asp |
| | | | | 485 | | | | | 490 | | | | | 495 | |
| Gly | Val | Met | Phe | Val | Asn | Tyr | Ser | Asn | Phe | Lys | Tyr | Thr | Asn | Ala | Ser |
| | | | 500 | | | | | 505 | | | | | 510 | | |
| Lys | Ser | Pro | Asn | Lys | Gly | Val | Gly | Val | Thr | Asn | Gly | Val | Ser | His | Leu |
| | | 515 | | | | 520 | | | | | 525 | | | | |
| Glu | Ala | Gly | Phe | Ser | Lys | Val | Ala | Val | Phe | Asn | Leu | Pro | Asn | Leu | Asn |
| | 530 | | | | 535 | | | | | 540 | | | | | |
| Asn | Leu | Ala | Ile | Thr | Ser | Val | Val | Arg | Arg | Asp | Leu | Glu | Asp | Lys | Leu |
| 545 | | | | | 550 | | | | | 555 | | | | | 560 |
| Ile | Ala | Lys | Gly | Leu | Ser | Pro | Gln | Glu | Ala | Asn | Lys | Leu | Val | Lys | Asp |
| | | | | 565 | | | | | 570 | | | | | 575 | |
| Phe | Leu | Ser | Ser | Asn | Lys | Glu | Leu | Val | Gly | Lys | Ala | Leu | Asn | Phe | Asn |
| | | | 580 | | | | | 585 | | | | | 590 | | |
| Lys | Ala | Val | Ala | Glu | Ala | Lys | Asn | Thr | Gly | Asn | Tyr | Asp | Glu | Val | Lys |
| | | 595 | | | | 600 | | | | | 605 | | | | |
| Arg | Ala | Gln | Lys | Asp | Leu | Glu | Lys | Ser | Leu | Lys | Lys | Arg | Glu | His | Leu |
| | 610 | | | | 615 | | | | | 620 | | | | | |
| Glu | Lys | Asp | Val | Ala | Lys | Asn | Leu | Glu | Ser | Lys | Ser | Gly | Asn | Lys | Asn |
| 625 | | | | | 630 | | | | 635 | | | | | | 640 |
| Lys | Met | Glu | Ala | Lys | Ala | Gln | Ala | Asn | Ser | Gln | Lys | Asp | Glu | Ile | Phe |
| | | | | 645 | | | | | 650 | | | | | 655 | |
| Ala | Leu | Ile | Asn | Lys | Glu | Ala | Asn | Arg | Asp | Ala | Arg | Ala | Ile | Ala | Tyr |
| | | | 660 | | | | | 665 | | | | | 670 | | |
| Ala | Gln | Asn | Leu | Lys | Gly | Ile | Lys | Arg | Glu | Leu | Ser | Asp | Lys | Leu | Glu |
| | | 675 | | | | | 680 | | | | | 685 | | | |
| Asn | Ile | Asn | Lys | Asp | Leu | Lys | Asp | Phe | Ser | Lys | Ser | Phe | Asp | Gly | Phe |
| | 690 | | | | | 695 | | | | | 700 | | | | |
| Lys | Asn | Gly | Lys | Asn | Lys | Asp | Phe | Ser | Lys | Ala | Glu | Glu | Thr | Leu | Lys |
| 705 | | | | | 710 | | | | | 715 | | | | | 720 |

```
Ala Leu Lys Gly Ser Val Lys Asp Leu Gly Ile Asn Pro Glu Trp Ile
            725                 730                 735

Ser Lys Val Glu Asn Leu Asn Ala Ala Leu Asn Glu Phe Lys Asn Gly
            740                 745                 750

Lys Asn Lys Asp Phe Ser Lys Val Thr Gln Ala Lys Ser Asp Gln Glu
            755                 760                 765

Asn Ser Ile Lys Asp Val Ile Asn Gln Lys Ile Thr Asp Lys Val
            770                 775                 780

Asp Glu Leu Asn Gln Ala Val Ser Val Ala Lys Ile Ala Cys Asp Phe
785                 790                 795                 800

Ser Gly Val Glu Gln Ala Leu Ala Asp Leu Lys Asn Phe Ser Lys Glu
            805                 810                 815

Gln Leu Ala Gln Gln Ala Gln Lys Asn Glu Ser Phe Asn Val Gly Lys
            820                 825                 830

Ser Glu Ile Tyr Gln Ser Val Lys Asn Gly Val Asn Gly Thr Leu Val
            835                 840                 845

Gly Asn Gly Leu Ser Gly Ile Glu Ala Thr Ala Leu Ala Lys Asn Phe
            850                 855                 860

Ser Asp Ile Lys Lys Glu Leu Asn Glu Lys Phe Lys Asn Phe Asn Asn
865                 870                 875                 880

Asn Asn Asn Asn Gly Leu Lys Asn Gly Gly Glu Pro Ile Tyr Ala Gln
                885                 890                 895

Val Asn Lys Lys Lys Thr Gly Gln Val Ala Ser Pro Glu Glu Pro Ile
            900                 905                 910

Tyr Ala Gln Val Ala Lys Lys Val Thr Lys Lys Ile Asp Gln Leu Asn
            915                 920                 925

Gln Ala Ala Thr Ser Gly Phe Gly Gly Val Gly Gln Ala Gly Phe Pro
930                 935                 940

Leu Lys Arg His Asp Lys Val Glu Asp Leu Ser Lys Val Gly Arg Ser
945                 950                 955                 960

Val Ser Pro Glu Pro Ile Tyr Ala Thr Ile Asp Asp Leu Gly Gly Ser
            965                 970                 975

Phe Pro Leu Lys Arg His Asp Lys Val Asp Asp Leu Ser Lys Val Gly
            980                 985                 990

Leu Ser Arg Asn Gln Glu Leu Thr Gln Lys Ile Asp Asn Leu Ser Gln
            995                 1000                1005

Ala Val Ser Glu Ala Lys Ala Gly Phe Phe Gly Asn Leu Glu Gln Thr
            1010                1015                1020

Ile Asp Lys Leu Lys Asp Phe Thr Lys Asn Asn Pro Val Asn Leu Trp
1025                1030                1035                1040

Ala Glu Ser Ala Lys Lys Val Pro Ala Ser Leu Ser Ala Lys Leu Asp
            1045                1050                1055

Asn Tyr Ala Thr Asn Ser His Thr Arg Ile Asn Ser Asn Ile Gln Asn
            1060                1065                1070

Gly Ala Ile Asn Glu Lys Ala Thr Gly Thr Glu Arg Gln Lys Asn Pro
            1075                1080                1085

Glu Trp Leu Lys Leu Val Asn Asp Lys Ile Val Ala His Asn Val Gly
            1090                1095                1100

Ser Val Pro Leu Ser Glu Tyr Asp Asn Ile Gly Phe Ser Gln Lys Asn
1105                1110                1115                1120

Met Lys Asp Tyr Ser Asp Ser Phe Lys Phe Ser Thr Lys Leu Asn Asn
            1125                1130                1135

Ala Val Lys Asp Ile Lys Ser Gly Phe Thr Gln Phe Leu Ala Asn Ala
```

-continued

```
                    1140                          1145                                1150
Phe  Ser  Thr  Gly  Tyr  Tyr  Ser  Met  Ala  Arg  Glu  Asn  Ala  Glu  His  Gly
               1155                     1160                     1165

Ile  Lys  Asn  Ala  Asn  Thr  Lys  Gly  Gly  Phe  Gln  Lys  Ser
     1170                     1175                    1180
```